US008471049B2

(12) United States Patent
Lei et al.

(10) Patent No.: US 8,471,049 B2
(45) Date of Patent: Jun. 25, 2013

(54) PRECURSORS FOR DEPOSITING GROUP 4 METAL-CONTAINING FILMS

(75) Inventors: Xinjian Lei, Vista, CA (US); Daniel P. Spence, Carlsbad, CA (US); Moo-Sung Kim, Sungnam (KR); Iain Buchanan, Stirling (GB); Laura M. Matz, Allentown, PA (US); Sergei Vladimirovich Ivanov, Schnecksville, PA (US)

(73) Assignee: Air Product and Chemicals, Inc., Allentown, PA (US)

( * ) Notice: Subject to any disclaimer, the term of this patent is extended or adjusted under 35 U.S.C. 154(b) by 520 days.

(21) Appl. No.: 12/629,416

(22) Filed: Dec. 2, 2009

(65) Prior Publication Data

US 2010/0143607 A1 Jun. 10, 2010

Related U.S. Application Data

(60) Provisional application No. 61/121,336, filed on Dec. 10, 2008.

(51) Int. Cl.
*C07F 7/28* (2006.01)
*C23C 16/00* (2006.01)

(52) U.S. Cl.
USPC ............... 556/40; 427/248.1; 106/287.19

(58) Field of Classification Search
USPC ............... 556/40; 106/287.19; 427/248.1
See application file for complete search history.

(56) References Cited

U.S. PATENT DOCUMENTS

| 5,767,302 | A | 6/1998 | Ogi et al. |
| 6,355,097 | B2 | 3/2002 | Itsuki et al. |
| 6,383,669 | B1 | 5/2002 | Leedham et al. |
| 6,562,990 | B1 | 5/2003 | St. Clair et al. |
| 6,623,656 | B2 * | 9/2003 | Baum et al. ............ 252/62.9 PZ |
| 6,743,933 | B2 | 6/2004 | Onozawa et al. |
| 6,841,817 | B2 | 1/2005 | Kurasawa et al. |
| 7,094,284 | B2 | 8/2006 | Baum et al. |
| 2002/0012819 | A1 | 1/2002 | Hideyuki et al. |
| 2007/0058415 | A1 | 3/2007 | Im et al. |
| 2007/0248754 | A1 | 10/2007 | Lei et al. |
| 2009/0136677 | A1 | 5/2009 | Lei et al. |
| 2009/0136685 | A1 | 5/2009 | Lei et al. |
| 2010/0119726 | A1 | 5/2010 | Lei et al. |

FOREIGN PATENT DOCUMENTS

| EP | 1 849 789 A1 | 10/2007 |
| EP | 1 983 073 A1 | 10/2008 |
| JP | 10114781 A2 | 5/1998 |
| JP | 2000100802 A2 | 9/1998 |
| JP | 2822946 B2 | 11/1998 |
| JP | 11092937 A2 | 4/1999 |
| JP | 2004059562 A2 | 2/2004 |
| JP | 2004-507551 | 3/2004 |
| JP | 2004-296522 | 10/2004 |
| JP | 2005-277426 | 10/2005 |
| JP | 2007-081410 | 3/2007 |
| KR | 2001-0084675 A | 9/2001 |
| KR | 2008-0021709 A | 3/2008 |
| WO | 8403042 | 8/1984 |
| WO | 01-99166 A1 | 12/2001 |
| WO | 02-18394 A1 | 3/2002 |
| WO | 2007002672 A2 | 1/2007 |

OTHER PUBLICATIONS

Robert C. Fay et al, Nuclear magnetic resonance studies of inversion and diketonate r-group exchange . . . , J. Am. Chem. Soc. 1983, 105, pp. 2118-2127.
Toshiyuki Fujimoto et al, Chemical reaction kinetics and growth rate of (Ba, Sr) Ti)3 Films . . . , J. of Electrochemical Soc. 2000, 147(7), pp. 2581-2588.
Hyun-Kyu Ryu et al, Thermal decomposition mechanism of Ti(O-iPr)2(DPM)2, J. of Electrochemical Soc. 1999, 146 (3) pp. 1117-1121.
Sung Taeg Hong et al, Study on the development of CVD Precursors I-synthesis and properties . . . , Bull. Korean Chem. Soc. 1996, vol. 17, No. 7, pp. 637-642.
Takayuki Watanabe et al, Liquid injection ALD of Pb(Zr,Ti)Ox thin films by a combination of self-regulating . . . J. Electrochemical Soc. 2007, 154 (12), pp. G262-G269.
U.B. Saxena, et al, Reactions of Zirconium Isopropoxide with B-Diketones and B-Keto-esters, J. Chem. Soc., 1970, 904-907.
Baunemann, A., et al; "Precursor Chemistry for TiO2: Titanium Complexes with a Mixed Nitrogen/Oxygen Ligand Sphere"; Dalton Transactions, No. 28; Apr. 27, 2006; pp. 3485-3490; XP-002569163.
Gordon, G., et al; "New Liquid Precursors for Chemical Vapor Deposition"; Mrs. 1997 Fall Proceedings—Symposium W—Chemical Aspects of Electronic Ceramics Processing; Vo. 495; 1997; pp. 63-68; XP-002569164.
Jones, et al; Molecular Design of Improved Precursors for the MOCVD of Oxides Used in Microelectronics Surface and Coatings Technology; vol. 201, No. 22-23; May 3, 2007; pp. 9046-9054; XP-022191932.

* cited by examiner

*Primary Examiner* — Porfirio Nazario Gonzalez
(74) *Attorney, Agent, or Firm* — Rosaleen P. Morris-Oskanian; Geoffrey L. Chase; Joseph D. Rossi

(57) ABSTRACT

Described herein are Group 4 metal-containing precursors, compositions comprising Group 4 metal-containing precursors, and deposition processes for fabricating conformal metal containing films on substrates. In one aspect, the Group 4 metal-containing precursors are represented by the following formula I:

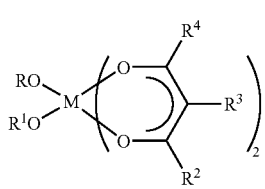

wherein M comprises a metal chosen from Ti, Zr, and Hf; R and $R^1$ are each independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups. Also described herein are methods for making Group 4 metal-containing precursors and methods for depositing films using the Group 4 metal-containing precursors.

18 Claims, 8 Drawing Sheets

PRECURSORS FOR DEPOSITING GROUP 4 METAL-CONTAINING FILMS

CROSS-REFERENCE TO RELATED APPLICATIONS

This application claims the benefit of U.S. Provisional Patent Application No. 61/121,336 filed 10 Dec. 2008.

BACKGROUND OF THE INVENTION

Disclosed herein are precursors and compositions thereof for depositing Group 4 metal-containing films. Also disclosed herein are methods for making the precursors along with methods for depositing Group 4 metal-containing films. With regard to the later, the described method may form a metal-containing film, such as, but not limited to, stoichiometric or non-stoichiometric strontium titanate and barium strontium titanate films using deposition processes such as, but not limited to, atomic layer deposition (ALD) or cyclic chemical vapor deposition (CCVD) that may be used, for example, as a gate dielectric or capacitor dielectric film in a semiconductor device.

With each generation of metal oxide semiconductor (MOS) integrated circuit (IC), the device dimensions have been continuously scaled down to provide for high-density and high-performance such as high speed and low power consumption requirements. Unfortunately, field effect semiconductor devices produce an output signal that is proportional to the width of the channel, such that scaling reduces their output. This effect has generally been compensated for by decreasing the thickness of gate dielectric, thus bringing the gate in closer proximity to the channel and enhancing the field effect which thereby increasing the drive current. Therefore, it has become increasingly important to provide extremely thin reliable and low-defect gate dielectrics for improving device performance.

For decades, a thermal silicon oxide, $SiO_2$ has been mainly used as a gate dielectric because it is stable with the underlying silicon substrate and its fabrication process is relatively simple. However, because the silicon oxide gate dielectric has a relatively low dielectric constant (k), 3.9, further scaling down of silicon oxide gate dielectric thickness has become more and more difficult, especially due to gate-to-channel leakage current through the thin silicon oxide gate dielectric.

This leads to consideration of alternative dielectric materials that can be formed in a thicker layer than silicon oxide but still produce the same or better device performance. This performance can be expressed as "equivalent oxide thickness (EOT)". Although the alternative dielectric material layer may be thicker than a comparative silicon oxide layer, it has the equivalent effect of a much thinner layer of silicon oxide layer.

To this end, high-k metal oxide materials have been proposed as the alternative dielectric materials for gate or capacitor dielectrics. Group 4-containing precursors may also be used by themselves or combined with other metal-containing precursors, such as, for example, $Pb(Zr,Ti)O_3$ or $(Ba,Si)(Zr,Ti)O_3$, to make high dielectric constant and/or ferroelectric oxide thin films. Because the dielectric constant of metal oxide materials can be made that is higher than that of the silicon oxide (e.g., a dielectric constant for $Al_2O_3$ ranging from 9-11; dielectric constant for $HfO_2$ ranging from 15-26; dielectric constant for $ZrO_2$ ranging from 14-25; dielectric constant from $TiO_2$ ranging from 50-80; and dielectric constant for $SrTiO_3$ or approximately 200), a thicker metal oxide layer having an EOT less than 2 Å can be deposited. As a result, the semiconductor industry requires Group 4 precursors, such as, for example, titanium-containing, zirconium-containing, and hafnium-containing precursors and combinations thereof, to be able to deposit metal-containing films such as, but not limited to, oxide, nitride, silicate or combinations thereof on substrates such as metal nitride or silicon.

Unfortunately, the use of high-k metal oxide materials presents several problems when using traditional substrate materials such as silicon. The silicon can react with the high-k metal oxide or be oxidized during deposition of the high-k metal oxide or subsequent thermal processes, thereby forming an interface layer of silicon oxide. This increases the equivalent oxide thickness, thereby degrading device performance. Further, an interface trap density between the high-k metal oxide layer and the silicon substrate is increased. Thus, the channel mobility of the carriers is reduced. This reduces the on/off current ratio of the MOS transistor, thereby degrading its switching characteristics. Also, the high-k metal oxide layer such as a hafnium oxide ($HfO_2$) layer or a zirconium oxide ($ZrO_2$) layer has a relatively low crystallization temperature and is thermally unstable. Thus, the metal oxide layer can be easily crystallized during a subsequent thermal annealing process for activating the impurities injected into source/drain regions. This can form grain boundaries in the metal oxide layer through which current can pass. As the surface roughness of the metal oxide layer increases, the leakage current characteristics may deteriorate. Further, the crystallization of the high-k metal oxide layer undesirably affects a subsequent alignment process due to irregular reflection of the light on an alignment key having the rough surface.

In addition to minimizing side reactions with the substrate that the Group 4 precursor is deposited upon, it is also desirable that the Group 4 precursor be thermally stable at a temperature of 250° C. or greater. Group 4-containing metal films are typically deposited using a vapor deposition (e.g., chemical vapor deposition and/or atomic layer deposition) process. It is desirable that these precursors are thermally stable during vapor delivery in order to avoid premature decomposition of the precursor before it reaches the vapor deposition chamber during processing. Premature decomposition of the precursor not only results in undesirable accumulation of side products that will clog fluid flow conduits of the deposition apparatus, but also may causes undesirable variations in composition of the deposited gate/capacitor dielectric, high dielectric constant and/or ferroelectric metal oxide thin film. Further, it is desirable that the Group 4 precursors avoid undesirable side reactions with other source reagents, e.g., reagents containing silicon, oxide, nitride, or other metals, such as, but not limited to, Pb and/or Ti. Because some of the Group 4 precursors are solid, it is desirable that these precursors maintain their chemical identity over time when dissolved or suspended in organic solvents. Any change in chemical identity of Group 4 precursor in the solvent medium is deleterious because it may impair the ability of the vapor deposition process to achieve repeatable delivery and film growth.

As previously discussed, the Group 4 precursors in the prior art are mostly solid and have relatively low vapor pressure (e.g., 0.5 torr or below). Of the few Group 4 precursors that are in liquid form that are reported in the prior art, these precursors are typically not thermally stable at temperatures greater than 100° C., which may cause delivery or process issues during semiconductor manufacturing which can include, but are not limited to, clogging of the delivery lines between the source container and reactor and unwanted particle deposition on the wafers.

Accordingly, there is a need to develop Group 4 precursors, preferably liquid Group 4 precursors, which exhibit at least one of the following properties: lower molecular weight (e.g., 500 m.u. or below), lower melting point (e.g., 100° C. or below), and higher vapor pressure (e.g., 0.5 torr or greater).

BRIEF SUMMARY OF THE INVENTION

Described herein are Group 4 metal-containing precursors and deposition processes for fabricating conformal metal containing films on substrates such as silicon, metal nitride and other metal layers using these organometallic precursors. Also described herein are methods for making Group 4 metal-containing precursors and methods for depositing films using the Group 4 metal-containing precursors.

In one embodiment, there is provided a method for forming a metal-containing film on at least a surface of the substrate that comprises: forming via vapor deposition the metal-containing film on the surface from a composition comprising Group 4 metal-containing precursor having the following formula I:

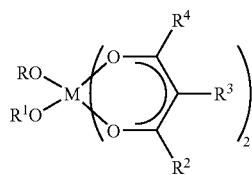

wherein M comprises a metal chosen from Ti, Zr and Hf; R and $R^1$ are each selected independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups; and wherein the vapor deposition is at least one selected from chemical vapor deposition, low pressure vapor deposition, plasma enhanced chemical vapor deposition, or atomic layer deposition. In this or other embodiments of the method, R and $R^1$ of Formula I can be either an isopropyl or a tent-butyl bulky alkyl group.

In a further embodiment, there is provided a composition for forming a metal-containing film comprising: at least 50 percent by weight or greater of at least one Group 4 metal-containing precursor having the following formula I:

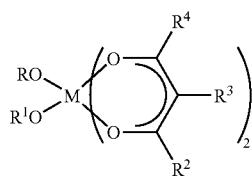

wherein M comprises a metal chosen from Ti, Zr, and Hf; R and $R^1$ are each independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups; and at least one solvent selected from the group consisting of: an aliphatic hydrocarbon, an aromatic hydrocarbon, an ether, an ester, a nitrite, an amine, an organic amide, an alcohol, an imine, a carbodiimide, a ketone, an aldehyde, an amidine, a guandadine, an isourea, a glyme solvent having from 1 to 6 oxygen atoms and mixtures thereof wherein the viscosity of the composition at a temperature of 25° C. is 50 centipoise or less.

In yet another embodiment, there is provided a composition comprising: a plurality of Group 4 metal-containing precursors wherein at least one of the Group 4 metal-containing precursors is a precursor having the following formula I:

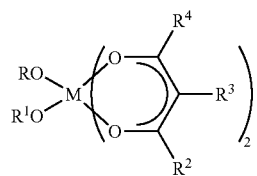

wherein M comprises a metal chosen from Ti, Zr and Hf; R and $R^1$ are each selected independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups; and wherein the at least one of the Group 4 metal-containing precursor having formula I is selected from the group consisting of: bis(ethoxy)bis(2,2,6,6-tetramethyl-3,5-heptanedionato)titanium; (ethoxy)(isoproxy)bis(2,2,6,6-tetramethyl-3,5-heptanedionato)titanium; bis(iso-propoxy)bis (2,2,6,6-tetramethyl-3,5-heptanedionato)titanium; (ethoxy) (t-butoxy)bis(2,2,6,6-tetramethyl-3,5-heptanedionato) titanium; bis(t-butoxy)bis(2,2,6,6-tetramethyl-3,5-heptanedionato)titanium; bis(iso-propoxy)bis(2,2-dimethyl-3,5-hexanedionato)titanium, (iso-proxy)(n-butoxy)bis(2,2-dimethyl-3,5-hexanedionato)titanium, bis(n-butoxy)bis(2,2-dimethyl-3,5-hexanedionato)titanium, and combinations thereof. In one particular embodiment, the composition comprises: bis(ethoxy)bis(2,2,6,6-tetramethyl-3,5-heptanedionato)titanium; (ethoxy)(isoproxy)bis(2,2,6,6-tetramethyl-3,5-heptanedionato)titanium; and bis(iso-propoxy)bis(2,2,6,6-tetramethyl-3,5-heptanedionato)titanium.

In a still further embodiment, there is provided a method for forming a metal-containing film on at least one surface of a substrate comprising: providing the at least one surface of the substrate in a deposition chamber; and forming the metal-containing film on the at least one surface by a deposition process chosen from a chemical vapor deposition process and an atomic layer deposition process from an at least one Group 4 metal-containing precursor having the following formula I:

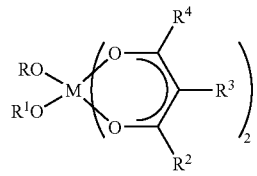

wherein M comprises a metal chosen from Ti, Zr, and Hf; R and $R^1$ are each independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups.

In another embodiment, there is provided a method for forming a metal-containing film on a substrate, the method comprising the steps of:

a. introducing a Group 4 metal-containing precursor having the following formula I into a deposition chamber and then chemisorbing the Group 4 metal onto at least a portion of the substrate which is heated;

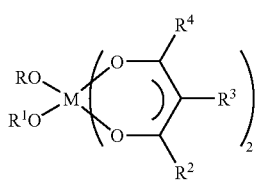

I wherein M comprises a metal chosen from Ti, Zr, and Hf; R and $R^1$ are each selected independently from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups b. purging away the unreacted Group 4 metal-containing precursor;

c. introducing a oxidizing agent comprising at least one selected from group consisting of water, oxygen, oxygen plasma, ozone, and water plasma;

d. introducing a polydentate β-ketoiminate selected from the group consisting of:

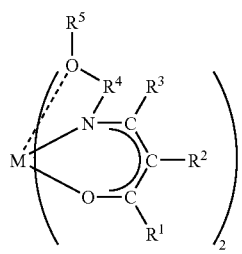

A wherein

M is a group 2 metal selected from the group consisting of: magnesium, calcium, strontium, and barium;

$R^1$ is selected from the group consisting of: a $C_1$ to $C_{10}$ alkyl, a $C_1$ to $C_{10}$ alkoxyalkyl, a $C_1$ to $C_{10}$ alkoxy, a $C_1$ to $C_{10}$ fluoroalkyl, a $C_3$ to $C_{10}$ cycloaliphatic, and a $C_6$ to $C_{10}$ aryl;

$R^2$ is selected from the group consisting of: hydrogen, a $C_1$ to $C_{10}$ alkyl, a $C_1$ to $C_{10}$ alkoxyalkyl, a $C_1$ to $C_{10}$ alkoxy, a $C_3$ to $C_{10}$ cycloaliphatic, and a $C_6$ to $C_{10}$ aryl;

$R^3$ is selected from the group consisting of: a $C_1$ to $C_{10}$ alkyl, a $C_1$ to $C_{10}$ alkoxyalkyl, a $C_1$ to $C_{10}$ alkoxy, a $C_3$ to $C_{10}$ cycloaliphatic, and a $C_6$ to $C_{10}$ aryl;

$R^4$ is a $C_1$ to $C_6$ linear or branched alkyl bridge; and $R^5$ is selected from the group consisting of: a $C_1$ to $C_{10}$ alkyl, a $C_1$ to $C_{10}$ fluoroalkyl, a $C_3$ to $C_{10}$ cycloaliphatic, and a $C_6$ to $C_{10}$ aryl, and;

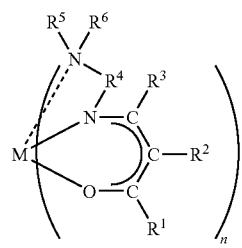

B wherein

M is a metal group having a valence of from 2 to 5;

$R^1$ is selected from the group consisting of alkyl, fluoroalkyl, cycloaliphatic, and aryl, having from 1 to 10 carbon atoms;

$R^2$ is selected from the group consisting of hydrogen, alkyl, alkoxy, cycloaliphatic, and aryl;

$R^3$ is selected from the group consisting of alkyl, fluoroalkyl, cycloaliphatic, and aryl;

$R^4$ is a linear or branched alkyl bridge;

$R^{5-6}$ are individually selected from the group consisting of alkyl, fluoroalkyl, cycloaliphatic, aryl, and heterocyclic containing either oxygen, or nitrogen atoms; and n is an integer equal to the valence of the metal M; and e. purging away the unreacted polydentate β-ketoiminate gas.

f. introducing a oxidizing agent selected from group consisting of: water, oxygen, oxygen plasma, ozone, and water plasma wherein steps a through f are repeated to deposit the metal-containing film. In one particular embodiment of the method, at least one of the precursor selected from the Group 4 precursor having the formula I, the polydentate β-ketoiminate, or both is dissolved in at least one solvent selected from the group consisting of: an aliphatic hydrocarbon, an aromatic hydrocarbon, an ether, an ester, a nitrile, an amine, an organic amide, an alcohol, an imine, a carbodiimide, a ketone, an aldehyde, an amidine, a guandadine, an isourea, a glyme solvent having from 1 to 6 oxygen atoms and mixtures thereof.

In another embodiment, there is provided a method for forming a metal-containing film on a substrate comprising: introducing a Group 4 metal-containing precursor represented by the formulas:

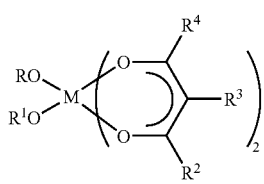

I wherein M comprises a metal chosen from Ti, Zr, and Hf; R and $R^1$ are each independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; and R⁴ is an alkyl group comprising from 1 to 6 carbon atoms and wherein $R^2$ and $R^4$ are different alkyl groups; and introducing at least one oxidizing agent into the deposition chamber wherein the at least one oxidizing agent reacts with the Group 4 metal-containing precursor to provide the metal-containing film on the substrate.

BRIEF DESCRIPTION OF SEVERAL VIEWS OF THE DRAWINGS

FIG. 1 shows that the first two precursors, or the Group 4 liquid-based metal-containing precursors described herein, are more volatile than the commerically available solid precursor.

FIG. 2 shows that the Group 4 metal-containing precursor described herein or bis(tert-butoxy)bis(2,2-dimethyl-3,5-hexanedionato)titanium is more stable and volatile than the precursor bis(tert-butoxy)bis(6-methyl-2,4-heptanedionato)titanium even through both precursors have the same molecular weight and are liquid at room temperature. This may indicate that the bulkier t-butyl $R^2$ group in bis(tert-butoxy)bis(2,2-dimethyl-3,5-hexanedionato)titanium—when compared to the iso-butyl $R^2$ group in bis(tert-butoxy)bis(6-methyl-2,4-heptanedionato)titanium—may prevent inter-molecular interactions in the liquid phase, thereby significantly increasing the stability of bis(tert-butoxy)bis(2,2-dimethyl-3,5-hexanedionato)titanium.

DETAILED DESCRIPTION OF THE INVENTION

Figure 1:
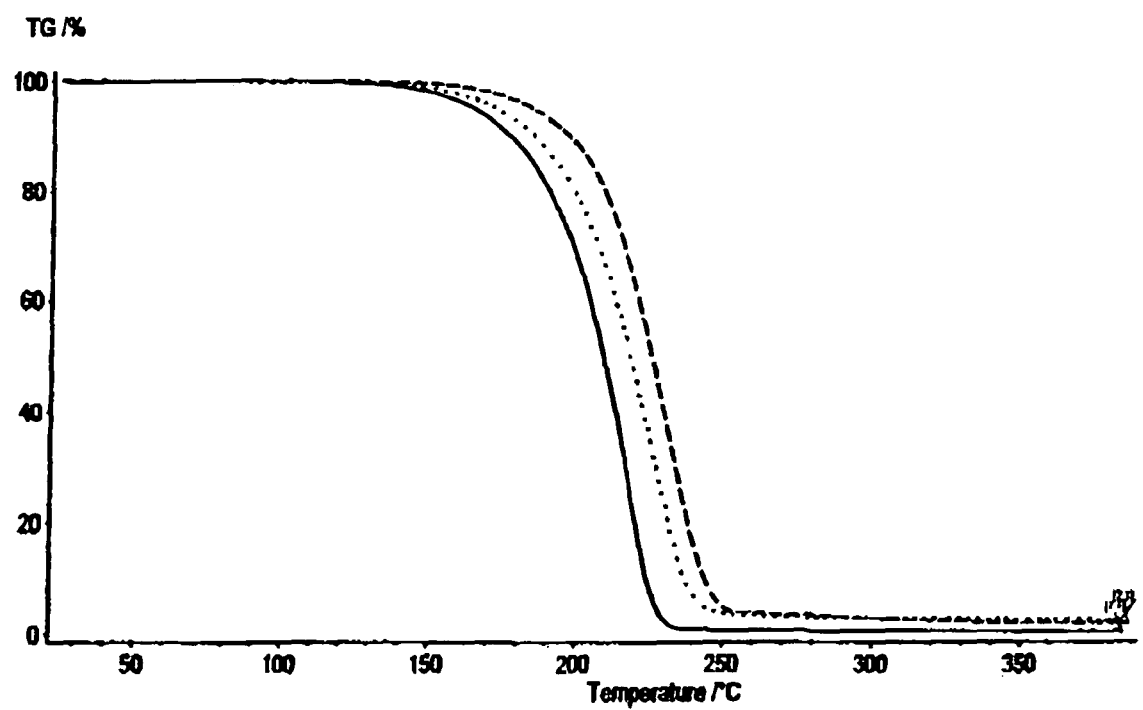
FIG. 1 provides the thermogravometric analysis (TGA) comparison for the evaporation of three Group 4 metal-containing precursors: bis(tert-butoxy)bis(2,2-dimethyl-3,5-hexanedionato)titanium (a liquid precursor described in Example 2, represented by the solid line), bis(iso-propoxy)bis(2,2-dimethyl-3,5-hexanedionato)titanium (a liquid precursor described in Example 1, represented by the dotted line), and a commercially available solid precursor bis(iso-propoxy)bis(2,2,6,6-tetramethyl-3,5-heptanedionato)titanium (provided by SAFC Hitech of Haverhill, Mass. and represented by the dashed line).
Figure 2:
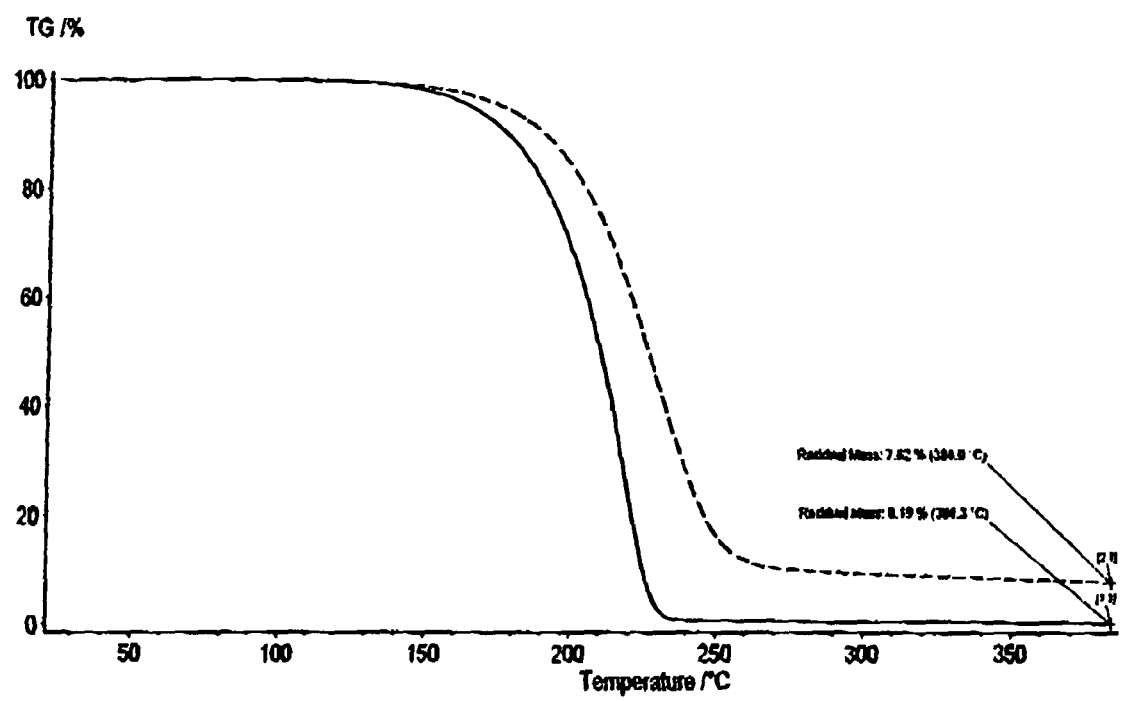
FIG. 2 provides the TGA comparison for the evaporation of bis(tert-butoxy)bis(2,2-dimethyl-3,5-hexanedionato)titanium (a liquid precursor described in Example 2, represented by the solid line) and bis(tert-butoxy)bis(6-methyl-2,4-heptanedionato)titanium (a liquid precursor described in Example 5, represented by the dashed line).
Figure 3:
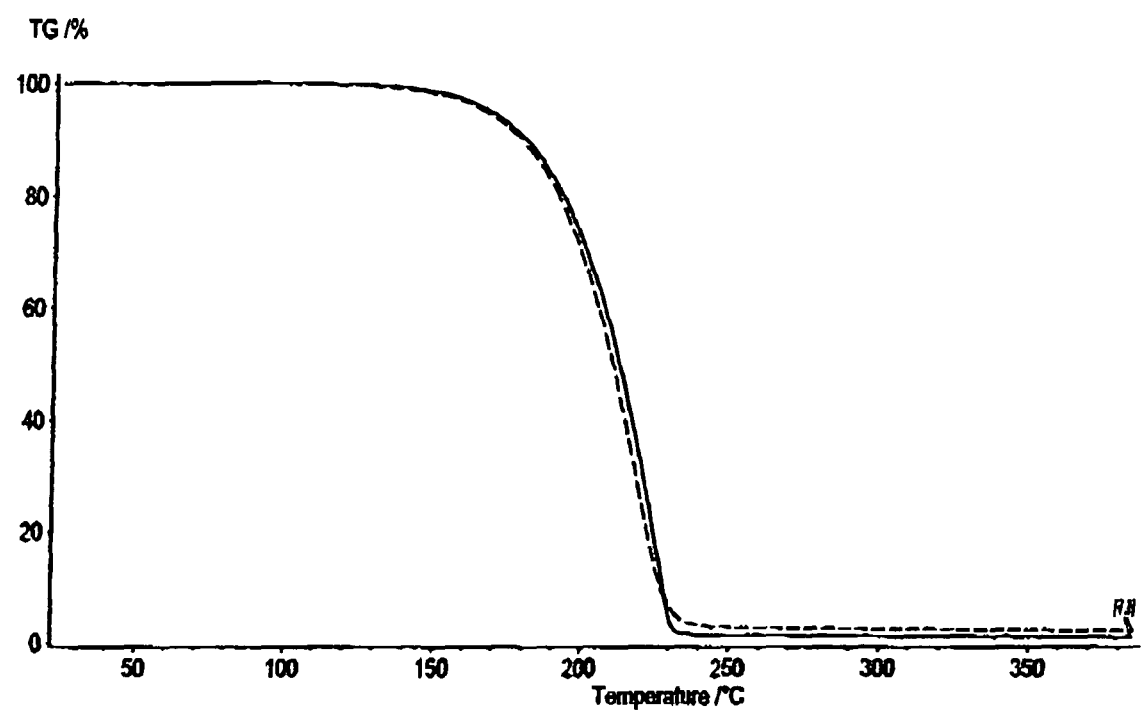
FIG. 3 provides the TGA comparison for the evaporation of bis(tert-butoxy)bis(2,2-dimethyl-3,5-hexanedionato)zirconium (a liquid precursor described in Example 3 and represented by the solid line) and bis(tert-butoxy)bis(2,2-dimethyl-3,5-hexanedionato)hafnium (a liquid precursor described in Example 4 and represented by the dashed line), which indicates that both precursors are volatile and can be used as precursor for CVD or ALD processes to deposit $ZrO_2$ or $HfO_2$, respectively.

Disclosed herein are Group 4 complexes that are suitable, for example, as precursors in chemical vapor deposition or other deposition processes. The complexes and compositions are useful for fabricating metal containing films on substrates such as silicon, metal nitride, metal oxide, metal oxynitride, metal silicate, and other metal containing layers via chemical vapor deposition (CVD) processes such as, but not limited to, atomic layer deposition (ALD) processes. The Group 4 metal containing precursors can also be used as dopants for other metal-containing films to introduce metal atoms such Ti, Hf, Zr, and combinations thereof into a material or film. As used herein, the term "chemical vapor depositon processes" refers to any process wherein a substrate is exposed to one or more volatile precursors, which react and/or decompose on the substrate surface to produce the desired deposition. The deposited metal films have applications ranging from computer chips, optical device, magnetic information storage, to metallic catalyst coated on a supporting material. Also disclosed herein are methods for preparing these complexes as well as their use in deposition processes, particularly CVD or ALD deposition processes.

The family of Group 4 precursors are represented by the following formula I:

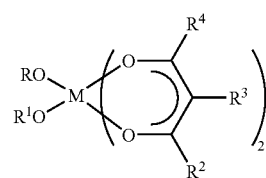

In formula I above, M comprises a metal chosen from Ti, Zr, and Hf; R and $R^1$ are each independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms.

In one particular embodiment, R and $R^1$ comprise a bulky alkyl group comprising from 3 to 5 carbon atoms; $R^2$ comprises a bulky alkyl group comprising from 4 to 6 carbon atoms; $R^3$ comprises hydrogen; and $R^4$ comprises a methyl group. In the latter embodiment of Formula I, R and $R^1$ can be either an isopropyl or a tert-butyl bulky alkyl group.

The term "alkyl" as used herein includes linear, branched, or cyclic alkyl groups, comprising from 1 to 10 carbon atoms, from 1 to 6 carbon atoms, from 1 to 3 carbon atoms, from 3 to 5 carbon atoms, from 4 to 6 carbons atoms, or variations of the foregoing ranges. Exemplary alkyl groups include, but are not limited to, methyl, ethyl, n-propyl, isopropyl, n-butyl, isobutyl, sec-butyl, tert-butyl, tert-amyl, n-pentyl, n-hexyl, cyclopentyl, and cyclohexyl. The term "alkyl" applies also to alkyl moieties contained in other groups such as haloalkyl, alkylaryl, or arylalkyl. The term "bulky" as used herein describes alkyl groups that are more sterically hindered compared to linear alkyl groups having the same number of carbon atoms and may include, for example, branched alkyl groups, cyclic alkyl groups, or alkyl groups having one or more side chains and/or substituents. The term "aryl" as used herein comprises 6 to 12 member carbon rings having aromatic character. Exemplary aryl groups include phenyl and napthyl groups. The term "alkyl-substituted aryl" applies to aryl moieties that are substituted with alkyl. Exemplary alkyl-substituted aryl groups include tolyl and xylyl groups. The term "halo" and "halogen" include fluorine, chlorine, bromine, or iodine. In certain embodiments, some of the groups discussed herein may be substituted with one or more other elements such as, for example, a halogen atom or other heteroatoms such as O, N, Si, or S.

In certain embodiments, at least one of $R^2$ and $R^4$ in the β-diketonate ligand of Formula I are different alkyl groups or is assymetrical. Examples of assymetrical β-diketonate ligands include, but are not limited to, 2,2-dimethylhexane-3,5-dione ("dmhd"), 6-methyl-2,4-hetanedione ("mhd") and 6-methoxy-5,5-dimethylhexane-2,4-dione ("methd").

In other embodiments, at least one of the $R^2$ and $R^4$ in the β-diketonate ligand are the same alkyl groups or is symmetrical. Examples of symmetrical β-diketonate ligands include, but are not limited to, 2,4-pentanedione ("acac"), 2,2,6,6-tetramethyl-3,5-heptanedionato ("thd"), 2,2,7-trimethyl-3,5-octanedionato ("tod") and 1,3-diphenylpropane-1,3-dione ("dbm").

In one particular embodiment, the Group 4 metal-containing precursor is a liquid which exhibits at least one of the following properties: lower molecular weight (e.g., 500 m.u. or below), lower melting point (e.g., 100° C. or below), and higher vapor pressure (e.g., 0.5 torr or greater). Exemplary melting point temperatures for the precursors disclosed herein include ranges having any one or more of the following endpoints: 100, 95, 90, 85, 80, 75, 70, 65, 60, 55, 50, 45, 40, 35, and/or 30° C. Examples of particular melting point ranges include, but are not limited to, 100° C. or less, 75° C. or less, or 60° C. or less.

In certain embodiments of the composition described herein, the composition comprises a plurality (e.g., two or more Group 4 metal-containing precursors). In this or other embodiments, at least one of the plurality of the Group 4 metal-containing precursors comprises a Group 4 metal-containing precursor having the formula I described herein. In one particular embodiment, the composition comprises the Group 4 metal-containing precursor wherein at least one of the Group 4 metal-containing precursor is selected from the group consisting of bis(ethoxy)bis(2,2,6,6-tetramethyl-3,5-heptanedionato)titanium; (ethoxy)(isoproxy)bis(2,2,6,6-tetramethyl-3,5-heptanedionato)titanium; bis(iso-propoxy)bis (2,2,6,6-tetramethyl-3,5-heptanedionato)titanium; (ethoxy)(t-butoxy)bis(2,2,6,6-tetramethyl-3,5-heptanedionato) titanium; bis(t-butoxy)bis(2,2,6,6-tetramethyl-3,5-heptanedionato)titanium; bis(iso-propoxy)bis(2,2-dimethyl-3,5-hexanedionato)titanium, (iso-proxy)(n-butoxy)bis(2,2-dimethyl-3,5-hexanedionato)titanium, bis(n-butoxy)bis(2,2-dimethyl-3,5-hexanedionato)titanium, and combinations thereof.

Also described herein is a method for making a Group 4 metal-containing oxide film, metal-containing nitride film, metal-containing oxynitride film, metal-containing silicate film, multi-component metal oxide film, and any combination or laminate thereof, which may be used, for example, in fabricating semiconductor devices. In one embodiment, the method disclosed herein provides a Group 4 metal or multi-component metal oxide film that has a dielectric constant substantially higher than that of either conventional thermal silicon oxide, silicon nitride, or zirconium/hafnium oxide dielectric.

The method disclosed herein deposits the Group 4 metal containing films using atomic layer deposition (ALD) or chemical vapor deposition (CVD) processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition (PECVD), high density chemical vapor deposition (PECVD), photon assisted chemical vapor deposition (PACVD), plasma-photon assisted chemical vapor deposition (PPECVD), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via plasma enhanced ALD (PEALD) or plasma enhanced cyclic CVD (PECCVD) process. In these embodiments, the deposition temperature may be relatively lower, or may range from 200° C. to 400° C., and may allow for a wider process window to control the specifications of film properties required in end-use applications. Exemplary deposition temperatures for the PEALD or PECCVD deposition include ranges having any one or more of the following endpoints: 200, 225, 250, 275, 300, 325, 350, 375, and/or 400° C.

In one embodiment of the method disclosed herein, a group 4 metal silicate or metal silicon oxynitride film is formed onto at least one surface of a substrate using a Group 4 metal-containing precursor having Formula I, a silicon-containing precursor, an oxygen source, and optionally a nitrogen source. Although metal-containing and silicon-containing precursors typically react in either liquid form or gas phase thereby preventing film formation, the method disclosed herein avoids pre-reaction of the metal containing and silicon-containing precursors by using ALD or CCVD methods that separate the precursors prior to and/or during the introduction to the reactor. In this connection, deposition techniques such as an ALD or CCVD processes are used to deposit the metal-containing film. For example, in certain embodiments, an A/D process is used to deposit the metal-containing film. In a typical ALD process, the film is deposited by exposing the substrate surface alternatively to the metal amide or the silicon-containing precursors. Film growth proceeds by self-limiting control of surface reaction, the pulse length of each precursor, and the deposition temperature. However, once the surface of the substrate is saturated, the film growth ceases. In yet another embodiment, the metal-containing film may be deposited using a CCVD process. In this embodiment, the CCVD process may be performed using a higher temperature range than the ALD window, or from 350° C. to 600° C. thereby preventing, for example, precursor decomposition. Exemplary deposition temperatures for the CCVD deposition include ranges having any one or more of the following endpoints (provided in degrees Celsius): 200, 225, 250, 275, 300, 325, 350, 375, 400, 425, 450, 475, 500, 525, 550, 575, and/or 600° C.

In certain embodiments, the method disclosed herein forms the multi-component metal oxide films using metal ketoiminate precursors and an oxygen source.

As mentioned previously, the method disclosed herein forms the metal-containing films using at least one metal precursor such as the Group 4 metal-containing precursors having formula I described herein, optionally at least one silicon-containing precursor, optionally an oxygen source, optionally an additional metal-containing or other metal-containing precursor precursor, optionally a reducing agent, and optionally a nitrogen source. Although the precursors and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator.

In certain embodiments, other metal-containing precursors can be used in addition to the Group 4 metal-containing precursors described herein. Metals commonly used in semiconductor fabrication include that can be used as the metal component for the metal amide includes: titanium, tantalum, tungsten, hafnium, zirconium, cerium, zinc, thorium, bismuth, lanthanum, strontium, barium, lead, and combinations thereof. Examples of other metal-containing precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTDMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, bis(2,2,6,6-tetramethyl-3,5-heptanedionato)strontium, bis(2,2,6,6-tetramethyl-3,5-heptanedionato)barium, $M(R_mC_{5-m-n}H_n)_2$ wherein M=Sr or Ba, n is a integer from 1 to 4, n+m=5, and combinations thereof.

In one embodiment, the metal-containing precursors, that can used in addition to the Group 4 metal precursors described herein to provide a metal-containing film, are polydentate β-ketoiminates which are found, for example, in Applicants' co-pending applications U.S. Publ. No. 2007/0248754A1, US Publ. No. 2009/0136677, and U.S. Publ. No. 2009/0136685, all of which are incorporated herein by reference in their entirety. In certain embodiments, the polydentate β-ketoiminates may incorporate an alkoxy group in the imino group. The polydentate β-ketoiminates are selected from the group represented by the following Structures A and B.

Structure A is defined as:

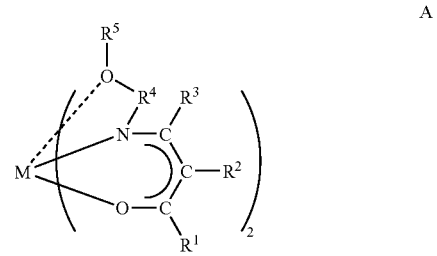

wherein M is a Group 2 metal such as, for example, magnesium, calcium, strontium, and barium. Preferably, M is strontium or barium. The organo groups (i.e., the R groups) employed in the complexes of the present invention may include a variety of organo groups and they may be linear or branched. In preferred embodiments, $R^1$ is selected from the group consisting of: a $C_1$ to $C_{10}$ alkyl, a $C_1$ to $C_{10}$ alkoxyalkyl, a $C_1$ to $C_{10}$ alkoxy, a $C_1$ to $C_{10}$ fluoroalkyl, a $C_1$ to $C_{10}$ cycloaliphatic, and a $C_6$ to $C_{10}$ aryl. As used herein, the group "alkoxyalkyl" refers to an ether-like moiety that includes a C—O—C fragment. Examples include —CH$_2$CH$_2$—O—CH$_2$CH$_2$—O—CH$_3$ and —CH$_2$CH$_2$—O—CH$_2$—O—CH$_3$. Preferably, $R^1$ is a bulky alkyl group containing 4 to 6 carbon atoms such as, for example, a tert-butyl group, a sec-butyl, and a tert-pentyl group. The most preferred $R^1$ group is tert-butyl or tert-pentyl. Preferably, $R^2$ is selected from the group consisting of: hydrogen, a $C_1$ to $C_{10}$ alkyl, a $C_1$ to $C_{10}$ alkoxyalkyl, a $C_1$ to $C_{10}$ alkoxy, a $C_3$ to $C_{10}$ cycloaliphatic, and a $C_6$ to $C_{10}$ aryl. More preferably, $R^2$ is hydrogen, or a $C_1$ to $C_2$ alkyl. Preferably, $R^3$ is selected from the group consisting of: a $C_1$ to $C_{10}$ alkyl, a $C_1$ to $C_{10}$ alkoxyalkyl, a $C_1$ to $C_{10}$ alkoxy, a $C_3$ to $C_{10}$ cycloaliphatic, and a $C_6$ to $C_{10}$ aryl. More preferably, $R^3$ is a $C_1$ to $C_2$ alkyl. Preferably, $R^4$ is a $C_1$ to $C_6$ linear or branched alkylene and, more preferably, $R^4$ contains a branched alkylene bridge containing 3 or 4 carbon atoms and having at least one chiral center carbon atom. Preferably, $R^5$ is selected from the group consisting of: a $C_1$ to $C_{10}$ alkyl, a $C_1$ to $C_{10}$ fluoroalkyl, a $C_3$ to $C_{10}$ cycloaliphatic, and a $C_6$ to $C_{10}$ aryl. More preferably, $R^5$ is a $C_1$ to $C_2$ alkyl.

Specific examples of these metal containing complexes are represented by the following structure B:

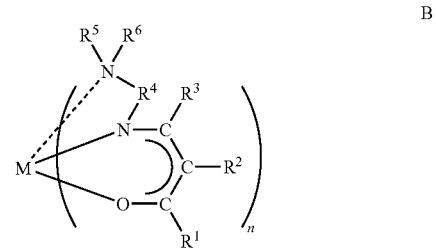

wherein M is a metal group having a valence of from 2 to 5 wherein $R^1$ is selected from the group consisting of alkyl, alkoxyalkyl, fluoroalkyl, cycloaliphatic, and aryl, having from 1 to 10 carbon atoms; $R^2$ is selected from the group consisting of hydrogen, alkyl, alkoxy, cycloaliphatic, and aryl; $R^3$ is selected from the group consisting of alkyl, alkoxyalkyl, fluoroalkyl, cycloaliphatic, and aryl; $R^4$ is a $C_{3-10}$ linear or branched alkyl bridge, preferably $R^4$ is having at least one chiral carbon atom; $R^{5-6}$ are individually selected from the group consisting of alkyl, fluoroalkyl, cycloaliphatic, aryl, and heterocyclic containing either oxygen, or nitrogen atoms; and n is an integer equal to the valence of the metal M.

In embodiments wherein the metal film deposited is a metal silicate, the deposition process further involves the introduction of at least one silicon-containing precursor. Examples of suitable silicon-containing precursors include a monoalkylaminosilane precursor, a hydrazinosilane precursor, or combinations thereof. In certain embodiments, the silicon-containing precursor comprises a monoalkylaminosilane precursor having at least one N—H fragment and at least one Si—H fragment. Suitable monoalkylaminosilane precursors containing both the N—H fragment and the Si—H fragment include, for example, bis(tert-butylamino)silane (BTBAS), tris(tert-butylamino)silane, bis(iso-propylamino)silane, tris(iso-propylamino)silane, and mixtures thereof. In one embodiment, the monoalkylaminosilane precursor has the formula $(R^5NH)_n SiR^6_m H_{4-(n+m)}$ wherein $R^5$ and $R^6$ are the same or different and independently selected from the group consisting of alkyl, vinyl allyl, phenyl, cyclic alkyl, fluoroalkyl, and silylalkyl and wherein n is a number ranging from 1 to 3, m is a number ranging from 0 to 2, and the sum of "n+m" is a number that is less than or equal to 3. In another embodiment, the silicon-containing precursor comprises a hydrazinosilane having the formula $(R^7_2N—NH)_x SiR^8_y H_{4-(x+y)}$ wherein $R^7$ and $R^8$ are same or different and independently selected from the group consisting of alkyl, vinyl, allyl, phenyl, cyclic alkyl, fluoroalkyl, silylalkyls and wherein x is a number ranging from 1 to 2, y is a number ranging from 0 to 2, and the sum of "x+y" is a number that is less than or equal to 3. Examples of suitable hydrazinosilane precursors include, but are not limited to, bis(1,1-dimethylhydrazino)-silane, tris(1,1-dimethylhydrazino)silane, bis(1,1-dimethylhydrazino)ethylsilane, bis(1,1-dimethylhydrazino)isopropylsilane, bis(1,1-dimethylhydrazino)vinylsilane, and mixtures thereof. Depending upon the deposition method, in certain embodiments, the silicon-containing precursor may be introduced into the reactor at a predetermined molar volume, or from about 0.1 to about 1000 micromoles. In this or other embodiments, the silicon-containing precursor may be introduced into the reactor for a predetermined time period, or from about 0.001 to about 500 seconds. The silicon-containing precursors react with the metal hydroxyl groups formed by the reaction of the metal amide with the oxygen source and become chemically adsorbed onto the surface of the substrate which results in the formation of a silicon oxide or a silicon oxynitride via metal-oxygen-silicon and metal-oxygen-nitrogen-silicon linkages, thus providing the metal silicate or the metal silicon oxynitride film.

Depending upon the deposition method, in certain embodiments, the one or more Group 4-metal containing precursor(s) or other precursors may be introduced into the reactor at a predetermined molar volume, or from about 0.1 to about 1000 micromoles. In this or other embodiments, the precursor(s) may be introduced into the reactor for a predetermined time period, or from about 0.001 to about 500 seconds.

As previously mentioned, some of the films deposited using the methods described herein (e.g., metal silicate or the metal silicon oxynitride films) may be formed in the presence of oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), NO, $N_2O$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In this or other embodiments wherein the film is deposited by an ALD process, the precursor pulse can have a pulse duration that is greater than 0.01 seconds, and the oxidant pulse duration can have a pulse duration that is greater than 0.01 seconds, while the water pulse duration can have a pulse duration that is greater than 0.01 seconds. In yet another embodiment, the purge duration between the pulses that can be as low as 0 seconds.

The deposition methods disclosed herein may involve one or more purge gases. The purge gas, which is used to purge away unconsumed reactants and/or reaction byproducts, is an inert gas that does not react with the precursors and may preferably be selected from the group consisting of Ar, $N_2$, He, $H_2$ and mixture thereof. In certain embodiments, a purge gas such as Ar is supplied into the reactor at a flow rate ranging from about 10 to about 2000 sccm for about 0.1 to 1000 seconds, thereby purging the unreacted material and any byproduct that remain in the reactor.

In certain embodiments, such as, for example, for those embodiments where a metal silicon oxynitride film is deposited, an additional gas such as a nitrogen source gas may be introduced into the reactor. Examples of nitrogen source gases may include, for example, NO, $NO_2$, ammonia, ammonia plasma, hydrazine, monoalkylhydrazine, dialkylhydrazine, and combinations thereof.

In certain embodiments of the method described herein, the temperature of the reactor or a deposition chamber may range from ambient temperature (e.g., 25° C.) to about 700° C. Exemplary reactor temperatures for the ALD or CVD deposition include ranges having any one or more of the following endpoints: 25, 50, 75, 100, 125, 150, 175, 200, 225, 250, 275, 300, 325, 350, 375, 400, 425, 450, 475, 500, 525, 550, 575, 600, 625, 650, 675, and/or 700° C. Examples of particular reactor temperature ranges include but are not limited to, 25° C. to 375° C., or from 75° C. to 700° C., or from 325° C. to 675° C. In this or other embodiments, the pressure may range from about 0.1 Torr to about 100 Torr or from about 0.1 Torr to about 5 Torr. In one particular embodiment, the dielectric film is deposited using a thermal CVD process at a pressure ranging from 100 mTorr to 600 mTorr. In another particular embodiment, the dielectric film is deposited using an ALD process at a temperature range of 1 Torr or less.

In certain embodiments of the method described herein, the temperature of the substrate in the reactor or a deposition chamber, may range from ambient temperature (e.g., 25° C.) to about 700° C. Exemplary substrate temperatures for the ALD or CVD deposition include ranges having any one or more of the following endpoints: 25, 50, 75, 100, 125, 150, 175, 200, 225, 250, 275, 300, 325, 350, 375, 400, 425, 450, 475, 500, 525, 550, 575, 600, 625, 650, 675, and/or 700° C. Examples of particular substrate temperature ranges include but are not limited to, 25° C. to 375° C., or from 75° C. to 700°

C., or from 325° C. to 675° C. In certain embodiments, the substrate temperature may be the same as or in the same temperature range as the reactor temperature during the deposition. In other embodiments, the substrate temperature differs from the reactor temperature during the deposition.

The respective step of supplying the precursors, the oxygen source, and/or other precursors or source gases may be performed by changing the time for supplying them to change the stoichiometric composition of the resulting metal silicate, metal silicon oxynitride film, or other metal-containing film.

Energy is applied to the at least one of the precursor, oxygen source gas, reducing agent, or combination thereof to induce reaction and to form the metal-containing film on the substrate. Such energy can be provided by, but not limited to, thermal, plasma, pulsed plasma, helicon plasma, high density plasma, inductively coupled plasma, X-ray, e-beam, photon, and remote plasma methods. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

In yet another embodiment of the method disclosed herein, the Group 4 metal-containing film is formed using a vapor deposition method that comprises the steps of: a. introducing a Group 4 metal-containing precursor in a vapor state into a deposition chamber and chemisorbing the metal-containing precursor onto a substrate which is heated; b. purging away the unreacted Group 4 metal-containing precursor; c. introducing an oxygen source onto the heated substrate to react with the sorbed Group 4 metal-containing precursor; and d. purging away the unreacted oxygen source. The above steps define one cycle for the method described herein; and the cycle can be repeated until the desired thickness of a metal-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and the oxygen source gases may be performed by varying the duration of the time for supplying them to change the stoichiometric composition of the resulting metal oxide film. For multi-component metal oxide films such as a strontium and barium containing film, a strontium-containing precursor, a barium-containing precursor or both precursors can be alternately introduced in step a into the reactor chamber.

The Group 4 metal-containing precursor and/or other metal containing precursors may be delivered to the deposition chamber such as a CVD or ALD reactor or reaction chamber in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Mn, to enable low volatility materials to be volumetrically delivered, leading to reproducible transport and deposition without thermal decomposition of the precursor.

In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate. For example, the solvent may be added to adjust the viscosity of the precursor composition, aid in the liquid delivery vaporization and/or transport of the specific metal precursor that is contained therein, solubilize the precursor(s) for use in a deposition process, or combinations thereof. In one particular embodiment, a direct liquid delivery method can be employed by dissolving the Group 4 metal-containing precursor described herein in a suitable solvent or a solvent mixture to provide a precursor composition wherein the precursor composition exhibits a viscosity of 50 centipoise (cP) or less at 25° C.

In certain embodiments, the precursor compositions comprises a solvent or mixture of solvents which include but are not limited to aliphatic hydrocarbons (e.g., $C_6$-$C_{12}$ aliphatic hydrocarbons such as hexane, heptane, octane, and/or pentane), aromatic hydrocarbons (e.g., $C_6$-$C_{18}$ aromatic hydrocarbons such as benzene, toluene, and/or mesitylene), ethers (e.g., dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound), esters, nitriles, alcohols (e.g., $C_2$-$C_{12}$ alkanols), amines (e.g., triethylamine and/or tert-butylamine), polyamines, amides, imines and carbodiimides (e.g., N,N'-diisopropylcarbodiimide), ketones, aldehydes, amidines, guanadines, and/or isoureas. Further examples of solvents include glyme solvents having from 1 to 6 oxygen atoms. In one particular embodiment, the solvent in the Group 4 metal precursor composition comprises an organic amide having the formula $R^9CONR^{10}R^{11}$ wherein $R^9$ and $R^{10}$ are each independently an alkyl group having from 1-10 carbon atoms and in certain embodiments can be connected to form a cyclic group $(CH_2)_n$, wherein n is from 4-6, and $R^{11}$ is selected from an alkyl having from 1 to 4 carbon atoms and a cycloalkyl group. Particular examples of amides having the formula $R^9CONR^{10}R^{11}$ include N-methyl- or N-ethyl- or N-cyclohexyl-2-pyrrolidinones, N,N-Diethylacetamide, and N,N-Diethylformamide.

In one particular embodiment, the precursor composition comprises a liquid-based Group 4 metal-containing precursor having a viscosity or 50 centipoise (cP) or less, or 45 cP or less, or 40 cP or less, of 35 cP or less, or 30 cP or less, or 25 cP or less, or 20 cP or less, or 15 cP or less, or a viscosity of 10 cP or less when measured at 25° C. In this or other embodiments, precursor composition comprises a liquid-based Group 4 metal-containing precursor having a viscosity of 50 cP or less at 25° C.; at least one Group 4 metal-containing precursor described herein but having a viscosity of 100 cP or greater at 25° C.; at least one solvent having a viscosity 5 cP or less at 25° C. and optionally an additional metal-containing precursor other than a Group 4 metal-containing precursor. In this embodiment, the total concentration of Group 4 metal-containing precursor is 50% by weight or greater, 55% by weight or greater, 60% by weight or greater, 65% by weight or greater, 70% by weight or greater, or 75% by weight or greater. Examples of at least one solvent for the precursor composition includes one or more of the solvents described herein such as, but not limited to, aliphatic hydrocarbons, aromatic hydrocarbons, linear or cyclic ethers, esters, nitriles, alcohols, amines, polyamines, organic amides, and combinations thereof. In one particular embodiment, the precursor composition comprises an aliphatic hydrocarbons such as octane.

In one embodiment of the method described herein, a cyclic deposition process such as CCVD, ALD, or PEALD may be employed, wherein a Group 4 metal-containing precursor or its solution and an oxygen source such as, for example, ozone, oxygen plasma or water plasma are employed. The gas lines connecting from the precursor canisters to the deposition chamber are heated to one or more temperatures ranging from about 110° C. to about 200° C. depending upon the process requirements, and the container of the Group 4 metal-containing precursor is kept at one or more temperatures ranging from about 100° C. to about 190° C. for bubbling whereas the solution comprising the Group 4 metal-containing precursor is injected into a vaporizer kept at one or more temperatures ranging from about 150° C. to about 200° C. for direct liquid injection. A flow of 100 to 1000 sccm of argon gas may be employed as a carrier gas to help deliver the vapor of the Group 4 metal-containing precursor to the deposition chamber during the precursor pulsing. The deposition chamber process pressure is about 1 Torr. In a typical ALD or CCVD process, the substrate such as silicon oxide or metal nitride are heated on a heater stage in a deposition chamber that is exposed to the Group 4 metal-containing precursor initially to allow the complex to chemically adsorb onto the surface of the substrate. An inert gas such as argon gas purges away unadsorbed excess complex from the process chamber. After sufficient Ar purging, an oxygen source is introduced into deposition chamber to react with the absorbed surface followed by another inert gas purge to remove reaction by-products from the chamber. The process cycle can be repeated to achieve the desired film thickness.

In another embodiment, the method described herein is a cyclic deposition process for the formation of ternary metal oxide films wherein a plurality of precursors are sequentially introduced into a deposition chamber, vaporized and deposited on a substrate under conditions for forming a said ternary metal oxide film.

In another embodiment, the resultant metal oxide films can be exposed to a post-deposition treatment such as, but not limited to, a plasma treatment, chemical treatment, ultraviolet light exposure, electron beam exposure, and/or other treatments to affect one or more properties of the film. In one particular embodiment, the film is exposed to a post-deposition treatment to densify it.

As mentioned previously, the method described herein may be used to deposit a metal-containing film onto at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and conducting metal layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes. Examples of suitable substrates include but are not limited to, semiconductor materials such as strontium titanate, barium strontium titanate, yttrium oxide doped with titanium, lanthanum oxide doped with titanium, and other lanthanide oxides doped with titanium The deposited dielectric films have applications which include but are not limited to computer chips, optical devices, magnetic information storages, coatings on a supporting material or substrate, microelectromechanical systems (MEMS), nanoelectromechanical systems, thin film transistor (TFT), and liquid crystal displays (LCD).

The following examples illustrate the method for preparing a Group 4 metal-containing precursor and depositing a film using the Group 4-metal-containing precursor described herein and are not intended to limit it in any way.

EXAMPLES

In the following examples, the G.C.M.S. Spectra for the examples were performed on a Hewlett Packard 5890 Series 11 G.C. and 5972 series mass selective detector with a HP-5MS. The NMR analyses for the examples were obtained on a Bruker AMX 500 spectrometer operating at 500 MHz. Chemical shifts were set from $C_6D_6$ at 7.16 ppm in $^1H$. The melting point measurements of certain compounds was obtained via differential scanning calorimetry (DSC) or thermal gravimetric analysis using Netzsch STA 449C under inert atmosphere with 100 standard cubic centimeters (sccm) dynamic flow of nitrogen and a ramp rate of 10° C./min.

Example 1

Synthesis of Bis(iso-propoxy)bis(2,2-dimethyl-3,5-hexanedionato)titanium ($R=R^1$=iso-propyl; $R^2$=t-butyl; $R^3$=H; $R^4$=methyl)

To a solution of 1.00 g (3.52 mmol) Ti(IV)isopropoxide in 20 mL tetrahydrofuran (THF) was added 1.00 g (7.04 mmol) 2,2-dimethyl-3,5-hexanedione (dmhd) in 5 mL THF to provide a reaction mixture. The resulting clear solution was heated to reflux for 16 hours. Removal of all volatiles from the reaction mixture generated a viscous brown oil weighing 1.50 g. The yield was 95%. $^1$H-NMR confirms no uncoordinated 2,2-dimethyl-3,5-hexanedione (dmhd) and shows the desired ratio of iPrO to dmhd coordinated to Ti being two iPrO's to two dmhd ligands. Elemental analysis: calculated for $Ti(Me_3CCOCHCOMe)_2(OCHMe_2)_2$: C, 58.93; H, 8.99. Found: C, 56.17; H, 7.98. $^1$H-NMR (500 MHz, $C_6D_6$) δ (ppm): 5.58 (CH), 5.04 (CH), 1.72 ($CH_3$), 1.40 [$(CH_3)_2$], 1.06 [$C(CH_3)_3$].

Example 2

Synthesis of Bis(tert-butoxy)bis(2,2-dimethyl-3,5-hexanedionato)titanium ($R=R^1$=tert-butyl; $R^2$=t-butyl; $R^3$=H; $R^4$=methyl)

Figure 4:
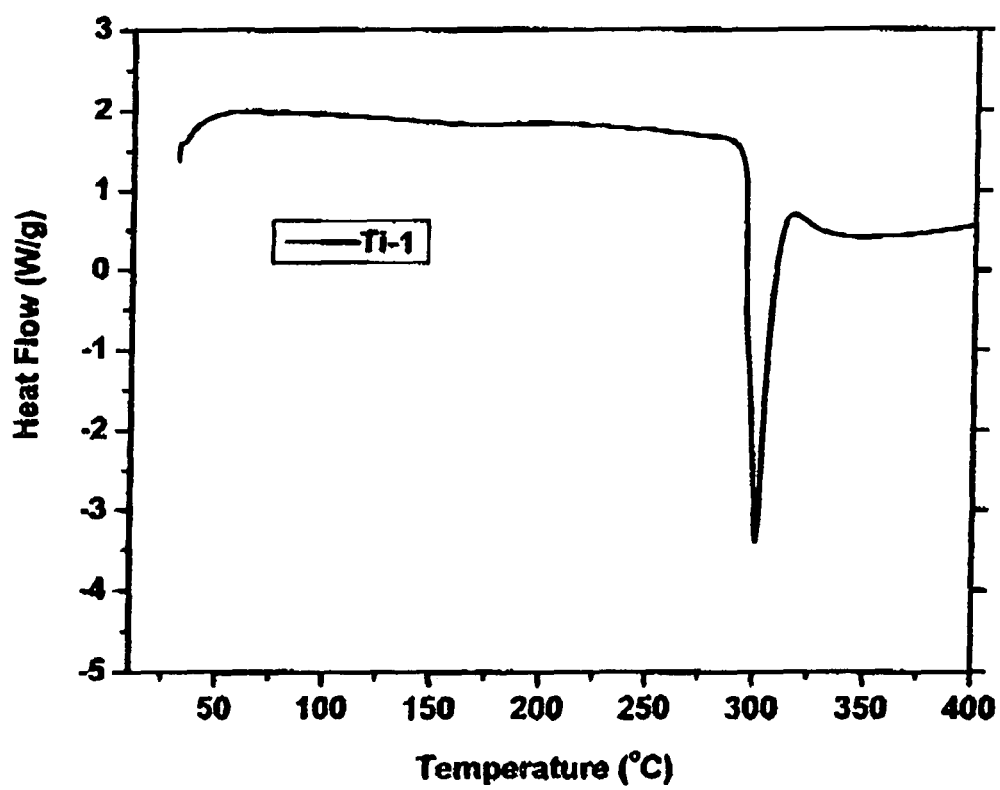
FIG. 4 provides the differential scanning calorimetry (DSC) measurement of bis(tert-butoxy)bis(2,2-dimethyl-3,5-hexanedionato)titanium of Example 2 and referred to as Ti-1, suggesting that Ti-1 is thermally stable in the liquid phase up to a temperature of at least 290° C.

To a solution of 1.10 g (3.23 mmol) Ti(IV)t-Butoxide in 20 mL THF was added 0.92 g (6.47 mmol) 2,2-dimethyl-3,5-hexanedione in 5 mL THF to provide a reaction mixture. The resulting yellow solution was refluxed for one hour. A viscous yellow-brown oil weighing 1.53 g was obtained after removal of all volatiles from the reaction mixture under vacuum. The yield was 99%. Elemental analysis: calculated for $Ti(Me_3CCOCHCOMe)_2(OCMe_3)_2$: C, 60.50; H, 9.31. Found: C, 59.83; H, 8.78. $^1$H-NMR (500 MHz, $C_6D_6$) δ (ppm): 5.57 (CH, dmhd), 1.73 ($CH_3$, dmhd), 1.49 ($OC(CH_3)_3$), 1.08 ($C(CH_3)_3$, dmhd). The DSC measurement of this Ti precursor—referred to as "Ti-1" in FIG. 4—shows that it is thermally stable in the liquid phase up to at least 290° C.

Example 3

Synthesis of Bis(tert-butoxy)bis(2,2-dimethyl-3,5-hexanedionato)zirconium ($R=R^1$=tert-butyl; $R^2$=t-butyl; $R^3$=H; $R^4$=methyl)

To a Solution of 1.00 g (2.61 Mmol) Zr(Iv)t-butoxide in 20 mL THF at room temperature was added 0.74 g (5.21 mmol) 2,2-dimethyl-3,5-hexanedione in 5 mL THE to provide a reaction mixture. The resulting reaction mixture was refluxed for one hour after which all volatiles were removed under vacuum yielding a viscous yellow oil weighing 1.319 with a yield of 96%. Elemental analysis calculated for Zr(Me$_3$CCOCHCOMe)$_2$(OCMe$_3$)$_2$: C, 55.45; H, 8.53. Found: C, 52.26; H, 7.28. $^1$H-NMR (500 MHz, O$_6$D$_6$) δ (ppm): 5.61 (CH, dmhd), 1.74 (CH$_3$, dmhd), 1.49 (OC(CH$_3$)$_3$), 1.14 (C(CH$_3$)$_3$, dmhd).

Example 4

Synthesis of Bis(tert-butoxy)bis(2,2-dimethyl-3,5-hexanedionato)hafnium (R=R$^1$=tert-butyl; R$^2$=t-butyl; R$^3$=H; R$^4$=methyl)

To a solution of 1.00 g (2.12 mmol) Hf(IV)t-butoxide in 20 mL THF at room temperature was added 0.60 g (4.25 mmol) 2,2-dimethyl-3,5-hexanedione in 5 mL THF to provide a reaction mixture. The resulting reaction mixture was refluxed for one hour after which all volatiles were evaporated under vacuum yielding a clear viscous oil weighing 1.26 g. The yield was 98%. Elemental analysis: calculated for Hf(Me$_3$CCOCHCOMe)$_2$(OCMe$_3$)$_2$: C, 47.48; H, 7.30. Found: C, 46.22; H, 6.60. $^1$H-NMR (500 MHz, C$_6$D$_6$) δ (ppm): 5.58 (CH, dmhd), 1.73 (CH$_3$, dmhd), 1.51 (OC(CH$_3$)$_3$), 1.13 (C(CH$_3$)$_3$, dmhd).

Example 5

Synthesis of Bis(tert-butoxy)bis(6-methyl-2,4-heptanedionato)titanium (R=R$^1$=tert-butyl; R$^2$=iso-butyl; R$^3$=H; R$^4$=methyl)

To a clear solution of 1.00 g (2.94 mmol) titanium (IV) t-butoxide in 20 mL THF was added 0.84 g (5.88 mmol) 6-methyl-2,4-heptanedione (mhd) in 5 mL THF to provide a reaction mixture. The resulting yellow reaction mixture was refluxed for one hour after which all volatiles was evaporated under vacuum yielding 1.33 g of dark green viscous oil. The yield was 95%. Elemental analysis: calculated for Ti(Me$_2$CHCH$_2$COCHCOMe)$_2$(OCMe$_3$)$_2$: C, 60.50; H, 9.31. Found: C, 56.80; N, H, 8.01. $^1$H-NMR (500 MHz, C$_6$D$_6$) δ (ppm): 5.34 (CH, mhd), 2.27-1.92 (CH$_2$,), 1.80-1.71 (CH$_3$, mhd), 1.54-1.52 (OC(CH$_3$)$_3$), 1.02 (CH(CH$_3$)$_2$, mhd), 0.88 ((CH$_3$)$_2$, mhd).

Example 6

Synthesis of Bis(methoxy)bis(2,2-dimethyl-3,5-hexanedionato)titanium (R=R$^1$=methyl; R$^2$=t-butyl; R$^3$=H; R$^4$=methyl)

To a white suspension of 1.00 g (5.81 mmol) titanium (IV) methoxide in 25 mL THF was added 1.65 g (11.62 mmol) 2,2-dimethyl-3,5-hexanedione in 5 mL THF to provide a reaction mixture. The resulting reaction mixture—which was a white slurry—was refluxed for one hour to produce a clear solution. Removal of all volatiles provided 2.23 g of a beige solid with a yield of 98%. DSC indicated it has a melting point of 65° C. Elemental analysis: calculated for Ti(Me$_3$CCOCHCOMe)$_2$(OMe)$_2$: C, 55.11; N, 0.00; H, 8.22. Found: C, 54.50; N, 0.18; H, 7.54. $^1$H-NMR (500 MHz, C$_6$D$_6$) δ(ppm): 5.59 (s, 1H), 4.43-4.39 (b, 3H), 1.81, 1.71 (two s, 3H), 1.22, 1.04 (two s, 9H).

Example 7

Synthesis of Bis(ethoxy)bis(2,2-dimethyl-3,5-hexanedionato)titanium (R=R$^1$=ethyl; R$^2$=t-butyl; R$^3$=H; R$^4$=methyl)

To a clear solution of 1.00 g (4.38 mmol) titanium (IV) ethoxide in 20 mL THF was added 1.25 g (8.77 mmol) 2,2-dimethyl-3,5-hexanedione in 5 mL THF to provide a reaction mixture. The reaction mixture—which was initially a clear solution—was heated to reflux for one hour after which THF was evaporated under vacuum to provide 1.81 g of a peach-brown colored oil. The yield was 98%. Elemental analysis: calculated for Ti(Me$_3$CCOCHCOMe)$_2$(OEt)$_2$: C, 57.14; H, 8.63. Found: C, 55.37; H, 7.71. $^1$H-NMR (500 MHz, C$_6$D$_6$) δ (ppm): 5.60 (s, 1H), 4.70 (b, 2H), 1.85, 1.73 (two s, 3H), 1.32 (b, 3H), 1.25, 1.04 (two s, 9H).

Example 8

Synthesis of Bis(iso-propoxy)bis(6-methyl-2,4-heptanedionato)titanium (R=R$^1$=iso-propyl; R$^2$=iso-butyl; R$^3$=H; R$^4$=methyl)

To a clear solution of 1.00 g (3.52 mmol) titanium (IV) isopropoxide in 20 mL THF was added 1.00 g (7.04 mmol) 6-methyl-2,4-heptanedione in 5 mL THF to provide a reaction mixture. The reaction mixture—which was initially clear—turned deep yellow to amber as the reaction progressed. All volatiles were evaporated from the reaction mixture under vacuum after refluxing for one hour which produced 1.55 g of dark amber viscous oil with a yield of 98%.

Example 9

Synthesis of Bis(n-propoxy)bis(2,2-dimethyl-3,5-hexanedionato)titanium (R=R$^1$=n-propyl; R$^2$=t-butyl; R$^3$=H; R$^4$=methyl)

To a clear solution of 6.34 g (22.30 mmol) of Titanium (IV) n-propoxide in 50 mL of hexanes at room temperature (e.g., approximately 25° C.) was added 6.34 g (44.60 mmol) of 2,2-dimethyl-3,5-hexanedione in 25 mL of hexanes dropwise. The reaction mixture was refluxed for 16 hours after which the volatiles were pumped off under vacuum. An oil was formed from the reaction mixture which was subjected to vacuum distillation heating at 160° C. under 125 mTorr vacuum to provide about 9.40 g of a yellow-green oil The yield was 94%. $^1$H-NMR (500 MHz, C$_6$D$_6$) δ(ppm): 5.59 (s, CH), 4.63 (b, OCH$_2$CH$_2$CH$_3$), 1.82, 1.72 (two s, CH$_3$), 1.72 (m, OCH$_2$CH$_2$CH$_3$), 1.25, 1.06 (two s, C(CH$_3$)$_3$), 1.02 (t, OCH$_2$CH$_2$CH$_3$).

Example 10

Synthesis of Bis(iso-butoxy)bis(2,2-dimethyl-3,5-hexanedionato)titanium (R=R$^1$=iso-butyl; R$^2$=t-butyl; R$^3$=H; R$^4$=methyl)

To a solution of 7.14 g (20.99 mmol) of Ti (IV) isobutoxide in 50 mL THF at room temperature was added 5.97 g (41.98 mmol) of 2,2-dimethyl-3,5-hexanedione in 25 mL THF drop wise. The reaction mixture was refluxed for 16 hours after which THF was pumped off under vacuum. An opaque peach colored oil was isolated which weighed 9.94 g. The crude oil was subjected to vacuum distillation by heating at 175° C. under 200 mTorr vacuum. Approximately 8.53 g of a viscous yellow oil was collected. The yield was 85%. $^1$H-NMR (500 MHz, $C_6D_6$) δ(ppm): 5.5 g (CH), 4.50 [$OCH_2CH(CH_3)_2$], 2.00 [$OCH_2CH(CH_3)_2$], 1.85-1.72 (three s) ($CH_3$), 1.26, 1.07 (two s) [($CH_3)_3$], 1.04 [$OCH_2CH(CH_3)_2$].

Example 11

Synthesis of Bis(tert-butoxy)bis(2,2-dimethyl-3,5-heptanedionato)titanium ($R=R^1=$tert-butyl; $R^2=$t-butyl; $R^3=$H; $R^4=$ethyl)

To a solution of 6.75 g (19.82 mmol) of Ti (IV) tert-butoxide in 65 mL of THF was added 6.19 g (39.64 mmol) of 2,2-dimethyl-3,5-heptanedione in 10 mL of THF drop wise at room temperature to provide a reaction mixture. The reaction mixture was refluxed for 16 hours after which THF was pumped off under vacuum. A pale yellow solid was isolated which weighed 9.98 g. DSC indicated it has a melting point of 113° C. The yield was 99.5%. $^1$H-NMR (500 MHz, $C_6D_6$) δ (ppm): 5.61-5.58 (four s) (CH), 2.17, 2.04 (two m) ($CH_2CH_3$), 1.50 [$OC(CH_3)_3$], 1.28, 1.10, 1.09 (three s) [($CH_3)_3$], 1.17, 0.96 (two m) ($CH_2CH_3$).

Example 12

Synthesis of Bis(iso-propoxy)bis(2,2-dimethyl-3,5-heptanedionato)titanium ($R=R^1=$iso-propyl; $R^2=$t-butyl; $R^3=$H; $R^4=$ethyl)

To a solution of 5.97 g (20.99 mmol) of Ti (IV) isopropoxide in 65 mL of THF was added 6.56 g (41.98 mmol) of 2,2-dimethyl-3,5-heptanedione in 10 mL of THF drop wise at room temperature. The reaction mixture was refluxed for 16 hours after which THF was pumped off under vacuum. A viscous amber oil was isolated which weighed 9.95 g. The yield was 99.5%. $^1$H-NMR (500 MHz, $C_6D_6$) δ(ppm): 5.61 (CH), 5.02 [$OCH(CH_3)_2$], 2.17, 2.02 (two m) ($CH_2CH_3$), 1.44-1.32 [$OCH(CH_3)_2$], 1.26, 1.07 (two s) [($CH_3)_3$], 1.16 (m), 0.94 (t) ($CH_2CH_3$).

Example 13

Synthesis of Bis(ethoxy)bis(2,2-dimethyl-3,5-heptanedionato)titanium ($R=R^1=$ethyl; $R^2=$t-butyl; $R^3=$H; $R^4=$ethyl)

To a solution of 5.09 g (20.30 mmol) of Ti (IV) ethoxide in 65 mL of THF was added 6.97 g (44.60 mmol) of 2,2-dimethyl-3,5-heptanedione in 10 mL of THF drop wise at room temperature. The reaction mixture was refluxed for 16 hours after which THF was pumped off under vacuum. An off white solid was isolated which weighed 9.83 g. The yield was 98.3%. DSC indicated it has a melting point of 46° C. $^1$H-NMR (500 MHz, $C_6D_6$) δ(ppm): 5.62 (CH), 4.69 ($OCH_2CH_3$), 2.14, 2.02 (two b) ($CH_2CH_3$), 1.32 ($OCH_2CH_3$), 1.24, 1.06 (two s) [($CH_3)_3$], 1.12, 0.94 (two b) ($CH_2CH_3$).

Example 14

Synthesis of Bis(tert-butoxy)bis(2,2,6-trimethyl-3,5-heptanedionato)titanium ($R=R^1=$t-butyl; $R^2=$t-butyl; $R^3=$H; $R^4=$iso-propyl)

To a tan-yellow solution of 6.39 g (18.78 mmol) of Ti (IV) tert-butoxide in 65 mL of THF, was added 6.39 g (37.55 mmol) of 2,2,6-trimethyl-3,5-heptanedione in 10 mL of THF drop wise at room temperature to provide a reaction mixture. The reaction mixture was heated to reflux for 16 hours after which THF was pumped off under vacuum. An off white solid was isolated which weighed 9.75 g. The yield was 97.5%. DSC indicated it has a melting point of 196° C. $^1$H-NMR (500 MHz, $C_6D_6$) δ(ppm): 5.63, 5.61 (two s) (CH), 2.39, 2.26 (two m) [$CH(CH_3)_2$], 1.49 [$OC(CH_3)_3$], 1.28, 1.10 [($CH_3)_3$], 1.22 (d), 1.06 (dd), 0.98 (dd) [$CH(CH_3)_2$].

Example 15

Synthesis of Bis(iso-propoxy)bis(2,2,6-trimethyl-3,5-heptanedionato)titanium ($R=R^1=$iso-propyl; $R^2=$t-butyl; $R^3=$H; $R^4=$iso-propyl)

To a solution of 5.63 g (19.82 mmol) of Ti (IV) isopropoxide in 65 mL of THF was added 6.75 g (39.64 mmol) of 2,2,6-trimethyl-3,5-heptanedione in 10 mL of THF drop wise at room temperature to provide a reaction mixture. Reaction mixture was refluxed for 16 hours after which the volatiles was pumped off under vacuum. A yellow-beige solid was isolated which weighed approximately 10 g. The yield was 100%. DSC indicated it has a melting point of 138° C. $^1$H-NMR (500 MHz, $C_6D_6$) δ(ppm): 5.65, 5.64 (two s) (CH), 4.98 [$OCH(CH_3)_2$], 2.38, 2.25 (two m) [$CH(CH_3)_2$], 1.39, 1.31 [$OCH(CH_3)_2$], 1.27, 1.08 (two s) [($CH_3)_3$], 1.21, 1.04, 0.96 (three d) [$CH(CH_3)_2$].

Example 16

Synthesis of Bis(ethoxy)bis(2,2,6-trimethyl-3,5-heptanedionato)titanium ($R=R^1=$ethyl; $R^2=$t-butyl; $R^3=$H; $R^4=$iso-propyl)

To a solution of 4.79 g (20.99 mmol) of Ti (IV) ethoxide in 65 mL of THF was added 7.15 g (41.98 mmol) of 2,2,6-trimethyl-3,5-heptanedione in 10 mL of THF drop wise at room temperature to provide a reaction mixture. The reaction mixture was heated to reflux for 16 hours after which the volatiles were pumped off under vacuum. A waxy burgundy solid was isolated which weighed 9.93 g. The yield was 99.3%. DSC indicated it had a melting point of 51° C. $^1$H-NMR (500 MHz, $C_6D_6$) δ(ppm): 5.66 (CH), 4.67 ($OCH_2CH_3$), 2.38, 2.24 (two m) [$CH(CH_3)_2$], 1.31 ($OCH_2CH_3$), 1.25, 1.07 (two s) [($CH_3)_3$], 1.19 (d), 1.03 (b), 0.91 (b) [$CH(CH_2)_2$].

Example 17

Synthesis of Bis(tert-butoxy)bis(2-acetylcyclohexanonato)titanium ($R=R^1=$t-butyl; $R^2$ and $R^3$ form a hexacyclic ring; $R^4=$methyl)

To a solution of 7.21 g (21.17 mmol) of Ti (IV) tert-butoxide in 50 mL THF at room temperature was added 5.93 g (42.33 mmol) of 2-acetylcyclohexanone in 25 mL THF drop wise to provide a reaction mixture. The reaction mixture was refluxed for four hours after which the volatiles were pumped off under vacuum. A burgundy brown waxy solid was obtained that was dissolved in hot hexanes for purification. Approximately 7.89 g of a light beige solid was isolated after the solution was kept at −40° C. The yield was 79%. DSC indicated it has a melting point of 84° C. $^1$H-NMR (500 MHz, $C_6D_6$) δ(ppm): 2.24-2.04 (three m) ($CH_2$), 1.84-1.77 (three s) ($CH_3$), 1.56 [$OC(CH_3)_3$], 1.35 ($CH_2$).

Example 18

Synthesis of Bis(iso-propoxy)bis(3-ethyl-2,4-pentanedionato)titanium (R==iso-propyl; $R^2$=methyl; $R^3$=methyl; $R^4$=methyl)

To a clear solution of 6.73 g (23.68 mmol) of Ti (IV) isopropoxide in 50 mL of THF was added 6.07 g (47.35 mmol) of 3-Ethyl-2,4-pentanedione in 25 mL THF drop wise at room temperature to provide a reaction mixture. The reaction mixture was refluxed for 16 hours after which the volatiles were pumped off under vacuum. Approximately 9.39 g of an orange amber oil was isolated. Attempts at purification via vacuum distillation resulted in decomposition of the product at temperatures in excess of 150° C. The yield was 20% after purification.

Example 19

Synthesis of Bis(iso-butoxy)bis(2,2,6,6-tetramethyl-3,5-heptanedionato)titanium (R=$R^1$=iso-butyl; $R^2$=t-butyl; $R^3$=H; $R^4$=t-butyl)

To a solution of 6.07 g (17.84 mmol) of Ti (IV) iso-butoxide in 50 mL THF at room temperature was added 6.57 g (35.67 mmol) of 2,2,6,6-tetramethyl-3,5-heptanedione in 25 mL THF drop wise to provide a reaction mixture. The reaction mixture was refluxed for 16 hours after which the volatiles were pumped off under vacuum. A white solid weighing 9.88 g was isolated. DSC of this white solid indicated it has a melting point of 154° C.

Example 20

Synthesis of Bis(ethoxy)bis(2,2,6,6-tetramethyl-3,5-heptanedionato)titanium

To a slightly yellow solution of 4.52 g (19.82 mmol) Ti (IV) ethoxide in 65 mL of THF was added 7.31 g (39.64 mmol) 2,2,6,6-tertamethyl-3,5-heptanedione in 10 mL of THF drop wise at room temperature. The reaction was heated to reflux for 16 hours after which all volatiles were pumped off under vacuum. 10 g of light green solid was isolated with a yield of 100%. TGA indicted it has a melting point of 40° C. $^1$H-NMR (500 MHz, $C_6D_6$) δ(ppm): 5.88 (CH), 4.64 ($OCH_2$), 1.29 ($OCH_2CH_3$), 1.25, 1.07 (two s) [$(CH_3)_3$].

Example 21

Synthesis of Composition comprising: bis(ethoxy)bis(2,2,6,6-tetramethyl-3,5-heptanedionato)titanium, (ethoxy)(isoproxy)bis(2,2,6,6-tetramethyl-3,5-heptanedionato)titanium, and bis(iso-propoxy)bis(2,2,6,6-tetramethyl-3,5-heptanedionato)titanium (R=$R^1$=ethyl; $R^2$=t-butyl; $R^3$=H; $R^4$=t-butyl; R=$R^1$=iso-propyl; $R^2$=t-butyl; $R^3$=H; $R^4$=t-butyl; and R=ethyl; $R^1$=iso-propyl; $R^2$=t-butyl; $R^3$=H; $R^4$=t-butyl)

To a clear solution of 5.00 g (21.92 mmol) titanium (IV) ethoxide containing 20% titanium (IV) iso-propoxide in 75 mL THF was added 8.08 g (43.83 mmol) 2,2,6,6-tetramethyl-3,5-heptanedione in 25 mL THF to provide a reaction mixture. The resulting reaction mixture which was a clear solution was heated to reflux for 16 hours after which the volatiles were evaporated under vacuum to provide 10.93 g of a pale yellow oil. The crude material was subjected to vacuum distillation heating at 160° C. under 150 mTorr vacuum. A slushy pink solid was transferred which weighed 7.85 g. The yield was 71%. DSC of the solid indicated it has a melting point of 33° C. NMR suggested the solid consists of a mixture of $Ti(OEt)_2(TMHD)_2$ (58% wt) $Ti(OEt)(OPr^i)(TMHD)_2$ (34% wt) and $Ti(OPr^i)_2(TMHD)_2$ (8% wt). By comparison, the melting point of pure commercial available $Ti(OPr^i)_2(TMHD)_2$ (see SAFC Hitech, product code TI-2-2) is >170° C. TGA indicated the mixture has similar vaporization characteristics of the pure $Ti(OPr^i)_2(TMHD)_2$.

Example 22

Synthesis of Bis(n-propoxy)bis(2,2,6,6-tetramethyl-3,5-heptanedionato)titanium (R=$R^1$=n-propyl; $R^2$=t-butyl; $R^3$=H; $R^4$=t-butyl)

To a clear solution of 5.34 g (18.78 mmol) of Titanium (IV) n-propoxide in 40 mL of hexanes at room temperature was added 6.92 g (37.55 mmol) of 2,2,6,6-tetramethyl-3,5-heptanedione in 10 mL of hexanes drop-wise to provide a reaction mixture. The reaction mixture was refluxed for 16 hours after which the volatiles were pumped off under vacuum. A white solid was isolated that was subjected to vacuum distillation heating at 180° C. under 125 mTorr vacuum. Approximately 9.53 g of a waxy pink solid was transferred. The yield was 95%. DSC of the solid indicated it has a melting point of 93° C. $^1$H-NMR (500 MHz, $C_6D_6$) δ(ppm): 5.89 (s, CH), 4.60 (t, $OCH_2CH_2CH_3$), 1.69 (m, $OCH_2CH_2CH_3$), 1.27, 1.08 (two s, $C(CH_3)_3$), 1.01 (t, $OCH_2CH_2CH_3$).

Example 23

Composition comprising: bis(iso-propoxy)bis(2,2-dimethyl-3,5-hexanedionato)titanium, (iso-proxy)(n-butoxy)bis(2,2-dimethyl-3,5-hexanedionato)titanium, and bis(n-butoxy)bis(2,2-dimethyl-3,5-hexanedionato)titanium (R=$R^1$=iso-propyl; $R^2$=t-butyl; $R^3$=H; $R^4$=t-butyl; R=$R^1$=n-butyl; $R^2$=t-butyl; $R^3$=H; $R^4$=t-butyl; and R=iso-propyl; $R^1$=n-butyl; $R^2$=t-butyl; $R^3$=H; $R^4$=t-butyl)

Figure 8:
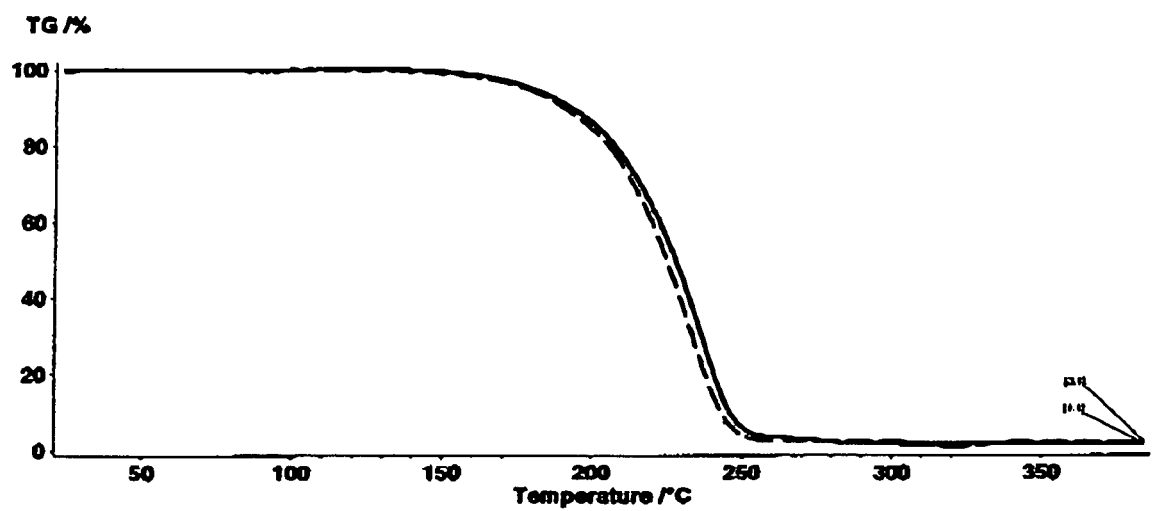
FIG. 8 is the TGA comparison for the evaporation of the low melting point composition that comprises three Group 4 precursors described herein and described in Example 21 versus a commercially available solid precursor bis(iso-propoxy)bis(2,2,6,6-tetramethyl-3,5-heptanedionato))titanium (provided by SAFC Hitech of Haverhill, Mass.), suggesting that the low melting point composition has similar vaporization characteristics to the high melting point solid.

To a clear solution of 5.71 g (18.29 mmol of titanium (IV) n-butoxy isopropoxide complexes containing a 2:1 ratio of iso-propoxy versus n-butoxy in 50 mL of hexanes at room temperature was added 5.20 g (36.59 mmol) of 2,2-dimethyl-3,5-hexanedione in 25 mL of hexanes. The reaction mixture was refluxed for 16 hours and then all volatiles were pumped off under vacuum. 8.21 g a yellow-green oil was isolated via vacuum distillation at 150° C. under 200 mTorr vacuum. The yield was 82%. NMR suggested it is a mixture containing a 1.4:1.2 ratio of iso-propoxy versus n-butoxy groups. $^1$H-NMR (500 MHz, $C_6D_6$) δ(ppm): 5.58 (s, CH), 5.05 (sp, $OCH(CH_3)_2$), 4.70 (b, $OCH_2CH_2CH_2CH_3$), 1:85-1.72 (three s, $CH_3$), 1.68 (m, $OCH_2CH_2CH_2CH_3$), 1.53 (m, $OCH_2CH_2CH_2CH_3$), 1.41-1.30 (m, $OCH(CH_3)_2$), 1.26, 1.06 (two s, $C(CH_3)_3$), 0.93 (t, $OCH_2CH_2CH_3$). TGA analysis of the precursor composition indicated it has similar vaporization characteristics of the commercially available precursor bis(iso-propoxy)bis(2,2-dimethyl-3,5-hexanedionato)titanium (see FIG. 8).

Example 24

Viscosity of bis(tert-butoxy)bis(2,2-dimethyl-3,5-hexanedionato)titanium (referred to herein as "Ti-1"), bis(iso-propoxy)bis(2,2-dimethyl-3,5-hexanedionato)titanium (referred to herein as "Ti-2") and precursor compositions comprising Ti-1 or Ti-2 and octane Viscosity of neat liquid samples (100 weight % ("wt. %")) of Ti-1, Ti-2 and precursor compositions comprising various wt. % of Ti-1 and Ti-2 and octane at 25° C. was measured using an AR-G2 rheometer (TA Instruments, New Castle, Del.) and results of the measurements are provided in Table 1. Temperature was controlled at desired temperature using a Peltier heating element. A 60 mm diameter parallel plate geometry was used. After sample loading, 600 seconds was allowed for thermal equilibration before shear rate sweep measurement. Viscosities were measured at shear rates ranging from 1 to 200 s$^{-1}$. All samples were Newtonian liquids. The viscosities are reported in the Table 1. Surprisingly, viscosity of solutions containing 75 wt % solutions of Ti-A was significantly less than 10 cP, and viscosity of 85 wt % solution of the Ti-2 in octane was 10.6 cP.

TABLE 1

Viscosity of neat Ti-1, Ti-2 and their solutions in octane

| Concentration of Precursor (Weight %) | Viscosity of Precursor Solution in cP at 25° C. Ti-1 | Viscosity of Precursor Solution in cP at 25° C. Ti-2 |
|---|---|---|
| 50 | 1.43 | 1.63 |
| 75 | 4.94 | NA |
| 85 | NA | 10.61 |
| 100 | 641 | 173 |

Example 25

Atomic Layer Deposition of Titanium Oxide Films Via Bubbling

Figure 5:
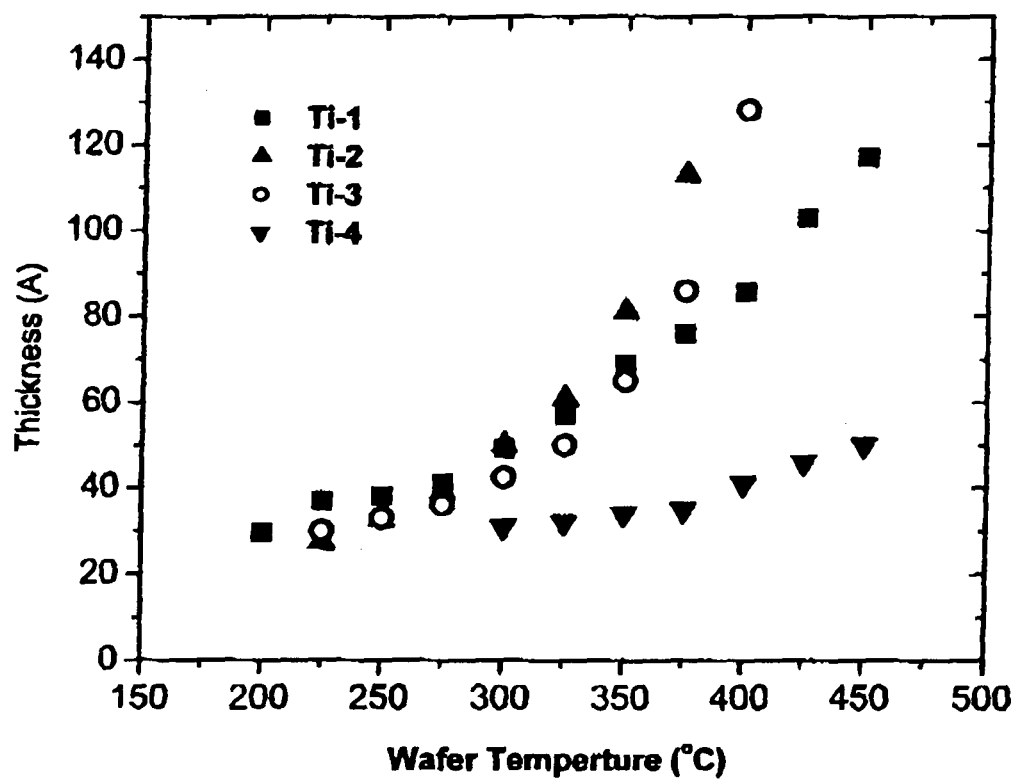
FIG. 5 is a graph of thickness versus temperature for the atomic layer deposition (ALD) of $TiO_2$ using liquid precursors including bis(tert-butoxy)bis(2,2-dimethyl-3,5-hexanedionato)titanium (of Example 2 and referred to on FIG. 5 as "Ti-1"), bis(iso-propoxy)bis(2,2-dimethyl-3,5-hexanedionato)titanium (of Example 1 and referred to on FIG. 5 as "Ti-2"), bis(iso-butoxy)bis(2,2-dimethyl-3,5-hexanedionato)titanium (of Example 10 and referred to on FIG. 5 as "Ti-3") and a commercially available solid precursor bis(iso-propoxy)bis(2,2,6,6-tetramethyl-3,5-heptanedionato))titanium (provided by SAFC Hitech of Haverhill, Mass., represented by the dashed line and referred to on FIG. 5 as "Ti-4"), suggesting that the liquid precursors are more reactive and may provide a relatively higher deposition rate.

Atomic layer depositions of TiO$_2$ films using titanium precursors described herein and a comparative titanium precursor and ozone as oxygen source were performed and the results are provided in FIG. 5. The substrates were bare silicon wafer cleaned with 1% HF solution, rinsed with deionized water and dried under nitrogen. As FIG. 5 shows, the deposition temperature ranged from approximately 200 to 450° C. The deposition chamber pressure was around 1.5 Torr. Containers containing the following titanium precursors: bis(tert-butoxy)bis(2,2-dimethyl-3,5-hexanedionato)titanium (referred to on FIG. 5 as Ti-1), bis(iso-propoxy)bis(2,2-dimethyl-3,5-hexanedionato)titanium (referred to on FIG. 5 as Ti-2), bis(iso-butoxy)bis(2,2-dimethyl-3,5-hexanedionato)titanium (referred to on FIG. 5 as Ti-3) and commercial available solid precursor bis(iso-propoxy)bis(2,2,6,6-tetramethyl-3,5-heptanedionato) (SAFC Hitech, product code Ti-2-2) (referred to on FIG. 5 as Ti-4) were maintained at 100 to 130° C., depending upon the precursor.

In the present example, one cycle of ALD or CCVD of TiO$_2$ was comprised of the following 4 steps:
1. Introduce the titanium precursor (Ti-1 through Ti-4) via bubbling with argon (Ar) as the carrier gas;
2. Ar purge to remove away any unsorbed titanium precursor with Ar;
3. Introduce ozone into the deposition chamber; and
4. Ar purge to remove away any unreacted ozone with Ar.

In this example, TiO$_2$ films are obtained, showing a deposition temperature dependence of the resulting TiO$_2$ film. The typical ALD conditions are: Ti precursor pulse time was 3 seconds, the Ar purge time after Ti precursor pulse was 8 seconds, the ozone pulse time was 5 seconds, and the Ar purge time after ozone pulse was 10 seconds. The cycle is repeated 100 times. The results are depicted in FIG. 5 in which the ALD process window was up to ~300° C.

Example 26

Atomic Layer Deposition of Titanium Oxide Films Via Direct Liquid Injection or Bubbling The present example illustrates that the ALD deposition results are substantially equivalent when delivering the same precursor in two different ways (e.g., bubbling and direct liquid injection system). Atomic layer depositions of TiO$_2$ films using the titanium precursor bis(ethoxy)bis(2,2,6,6-dimethyl-3,5-heptanedionato)titanium using two different vapor delivery methods are presented in FIG. 6. The ALD deposition results of the precursor bis(ethoxy)bis(2,2,6,6-dimethyl-3,5-heptanedionato)titanium described in Example 25 are presented on FIG. 6 as "Ti-5".

Figure 6:
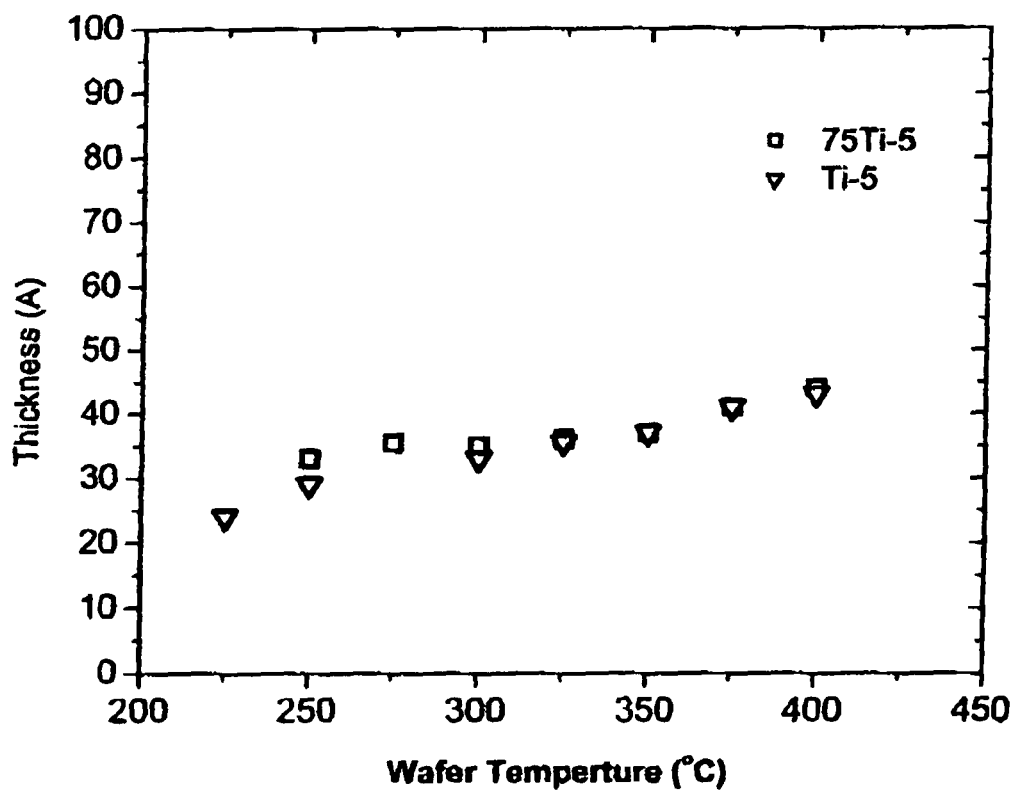
FIG. 6 is a graph of thickness versus temperature for the atomic layer deposition (ALD) of $TiO_2$ using the precursor bis(ethoxy)bis(2,2,6,6-dimethyl-3,5-heptanedionato)titanium which is delivered using two different vapor delivery methods: bubbling delivered neat (referred to on FIG. 6 as "Ti-5") and direct liquid injection or DLI (referred to on FIG. 6 as "75Ti-5") (delivered in a 75 weight % solution with octane). The data demonstrated both delivery methods provide similar ALD results.

The DLI deposition results wherein the precursor composition comprises 75 weight percent bis(ethoxy)bis(2,2,6,6-dimethyl-3,5-heptanedionato)titanium and 25 weight percent octane are identified on FIG. 6 as "75Ti-5". The dip tube side of the canister containing 75% wt of Ti-5 is connected to an injector valve in the DLI system and ~30 psig of nitrogen is connected to the other side of the canister to push the liquid. The Ti solution was pushed through an liquid flow controller (LFC) with a flow rate of 75 mg/min into the vaporizer set at 140° C. via an injection valve. This injection valve was always open. The Ti solution was vaporized in the vaporizer and the resulting Ti containing vapor was either delivered into the reactor chamber during the Ti pulse or diverted into exhaust during other pulses. The deposition temperature range is 200~400° C. The deposition chamber pressure ranges around 1.5 Torr, depending upon the gas flow rates. DLI requires an additional step to inject liquid whereas bubbling 4 steps.

One cycle of ALD wherein the precursor is delivered via DLI comprised the following 5 steps.
1. Injection of the titanium precursor composition; opening an injection valve for a few milliseconds will provide titanium precursor containing vapor in the vaporizor;
2. Titanium pulse; Introducing tianium precursor vapor to the deposition chamber; and titanium precursor is chemically sorbed on the heated substrate;
3. Ar purge; Purging away any unsorbed titanium precursor with Ar;
4. O$_3$ pulse; Introducing O$_3$ into the deposition and,
5. Ar purge; Purging away any unreacted O$_3$ with Ar.

In this example, TiO$_2$ films are obtained, showing a deposition temperature dependence of the resulting TiO$_2$ film. The typical ALD conditions are: the injection rate of the sultion was 75 mg/min, Ti precursor pulse time was 4 seconds, the Ar purge time after Ti precursor pulse was 8 seconds, the ozone pulse time was 5 seconds, and the Ar purge time after ozone pulse was 10 seconds. The cycle is repeated 100 times. The results are depicted in FIG. 6 in which the ALD process window was up to ~300° C.

Example 27

Atomic Layer Deposition of Strontium Titanate Films

This example describes an ALD or CCVD deposition of strontium titanate using a titanium complex illustrated in examples described above as titanium precursor bis(tert-butoxy)bis(2,2-dimethyl-3,5-hexanedionato)titanium (referred to herein as Ti-1) (delivered neat via bubbling), a strontium precursor (bis(2,2-dimethyl-5-(1-dimethylamino-2-propylimino)-3-hexanonato-N,O,N')strontium) dissolved in solvent [(0.1M in 10% wt THF in dedocane), and ozone as oxygen source. The deposition temperature was approximately 300° C. The deposition chamber pressure was approximately 1.5 Torr. The strontium titanate film can be formed with combination of $TiO_2$ and SrO subcycles. Strontium delivered via DLI.

One subcycle of ALD or CCVD of $TiO_2$ comprised the following 4 steps.
1. Introduce the titanium precursor via bubbling with Ar as carrier gas (Ti precursor pulse);
2. Ar purge to remove away any unsorbed titanium precursor with Ar (Ar purge);
3. Introduce ozone into the deposition chamber ($O_3$ pulse), and;
4. Ar purge to remove away any unreacted ozone with Ar (Ar purge).

One subcycle of A/D or CCVD of SrO comprised the following 4 steps.
1. Introduce the Strontium precursor via vaporizer with Ar as carrier gas (Sr precursor pulse);
2. Ar purge to remove away any unsorbed strontium precursor with Ar (Sr purge);
3. Introduce ozone into the deposition chamber ($O_3$ pulse), and;
4. Ar purge to remove away any unreacted ozone with Ar (Ar purge).

Figure 7:
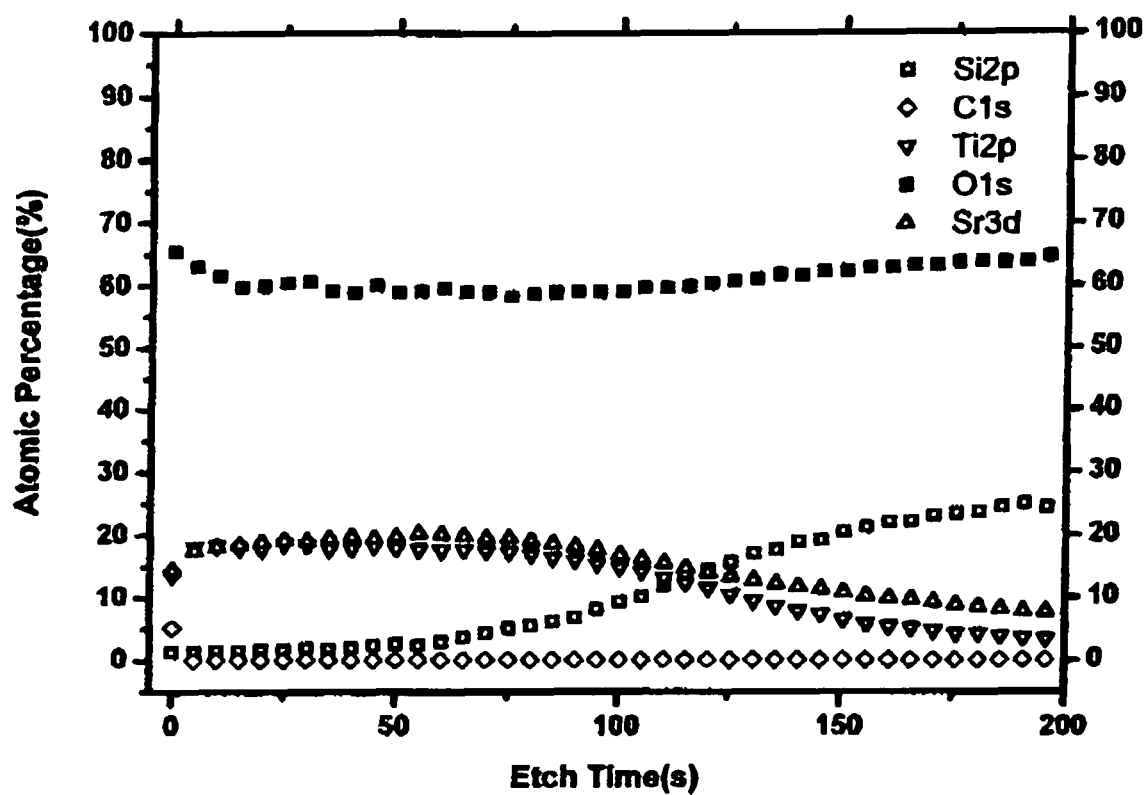
FIG. 7 is an X-ray Photoelectron Spectroscopy (XPS) analysis of strontium titanate films, deposited using the Ti-containing precursor bis(tert-butoxy)bis(2,2-dimethyl-3,5-hexanedionato)titanium (of Example 2 and referred to herein as Ti-1) indicating that there is no carbon contamination and a stoichiometric STO film can be formed.

In present example, a stoichiometric STO film can be formed with 5 subcycles of $TiO_2$+5 subcycles of SrO which is repeated by 40 cycles. Each step times of one $TiO_2$ subcycle are 3 seconds (Ti precursor pulse), 5 seconds (Ar purge), 5 seconds ($O_3$ pulse) and 5 seconds (Ar purge). Each step times of SrO subcycle are 5 seconds (Sr precursor pulse), 5 seconds (Ar purge), 5 seconds ($O_3$ pulse) and 5 seconds (Ar purge). The resulting film was analyzed by XPS as depicted in FIG. 7, showing a stoichiometric STO film can be formed.

The invention claimed is:

1. A method for forming a metal-containing film on at least a surface of a substrate comprising:
    forming via vapor deposition the metal-containing film on the surface from a composition comprising Group 4 metal-containing precursor having the following formula I:

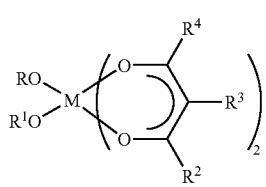

wherein M is Ti; R and $R^1$ are each independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups; and
    at least one solvent selected from the group consisting of: an aliphatic hydrocarbon, an aromatic hydrocarbon, an ether, an ester, a nitrite, an amine, an organic amide, an alcohol, an imine, a carbodiimide, a ketone, an aldehyde, an amidine, a guandadine, an isourea, a glyme solvent having from 1 to 6 oxygen atoms and mixtures thereof wherein the viscosity of the composition at a temperature of 25° C. is 50 centipoise or less,
    wherein the vapor deposition is at least one selected from cyclic chemical vapor deposition, plasma enhanced chemical vapor deposition, or atomic layer deposition.

2. The method of claim 1 wherein $R^2$ comprises a tert-butyl group, $R^4$ comprises a methyl group, and $R^3$ comprises hydrogen.

3. The method of claim 2 wherein R and $R^1$ each comprise a tert-butyl group.

4. The method of claim 2 wherein R and $R^1$ each comprise an ethyl group.

5. The method of claim 2 wherein R and $R^1$ each comprise an iso-propyl group.

6. The method of claim 1 wherein $R^2$ comprises an iso-butyl group, $R^4$ comprises a methyl group, and $R^3$ comprises hydrogen.

7. The method of claim 6 wherein R and $R^1$ each comprise a tert-butyl group.

8. The method of claim 6 wherein R and $R^1$ each comprise an ethyl group.

9. The method of claim 6 wherein R and $R^1$ each comprise an iso-propyl group.

10. The method of claim 1 wherein the metal-containing precursor has a melting point of 60° C. or below.

11. A composition for forming a metal-containing film comprising:
    at least 50 percent by weight or greater of at least one Group 4 metal-containing precursor having the following formula I

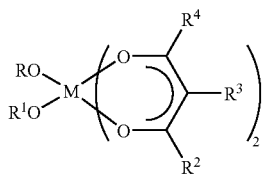

wherein M is Ti; R and $R^1$ are each independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups; and
    at least one solvent selected from the group consisting of: an aliphatic hydrocarbon, an aromatic hydrocarbon, an ether, an ester, a nitrite, an amine, an organic amide, an alcohol, an imine, a carbodiimide, a ketone, an aldehyde, an amidine, a guandadine, an isourea, a glyme solvent having from 1 to 6 oxygen atoms and mixtures thereof wherein the viscosity of the composition at a temperature of 25° C. is 50 centipoise or less.

12. The composition of claim 11 wherein the at least one solvent is selected from the group consisting of: the ether selected from the group consisting of glyme solvents having from 1 to 6 oxygen atoms; the alcohol comprising $C_2$-$C_{12}$ alkanols, the ether selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed Ci range is the number i of carbon atoms in the ether compound and the suffixed Oi range is the number i of oxygen atoms in the ether compound; the hydrocarbons comprising $C_6$-$C_{12}$ aliphatic hydrocarbons; the hydrocarbons comprising $C_6$-$C_{18}$ aromatic hydrocarbons; an organic amide of the form RCONR'R" wherein R and R' are alkyl groups comprising from 1 to 10 carbon atoms and can be can be connected to form a cyclic group $(CH_2)_n$, wherein n is from 4 to 6, and R" is selected from an alkyl group comprising from 1 to 4 carbon atoms and an cycloalkyl group.

13. The composition of claim 12 wherein the at least one solvent comprises at least one selected from the group consisting of octane, dodecane, toluene, and mesitylene.

14. The composition of claim 11 wherein the viscosity is 25 cP or less at 25° C.

15. The composition of claim 14 wherein the viscosity is 10 cP or less at 25° C.

16. A composition comprising:
a plurality of Group 4 metal-containing precursors wherein at least one of the Group 4 metal-containing precursors is a precursor having the following formula I:

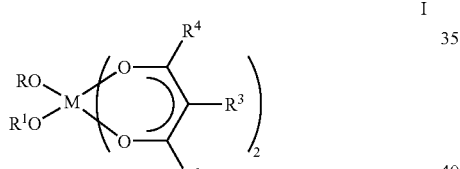

I wherein M comprises a metal chosen from Ti, Zr and Hf; R and $R^1$ are each independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups; and wherein the at least one of the Group 4 metal-containing precursor having formula I is selected from the group consisting of bis(iso-propoxy)bis(2,2-dimethyl-3,5-hexanedionato)titanium, (iso-proxy)(n-butoxy)bis(2,2-dimethyl-3,5-hexanedionato)titanium, and bis(n-butoxy)bis(2,2-dimethyl-3,5-hexanedionato)titanium.

17. A composition comprising:
a plurality of Group 4 metal-containing precursors wherein at least one of the Group 4 metal-containing precursors is a precursor having the following formula I:

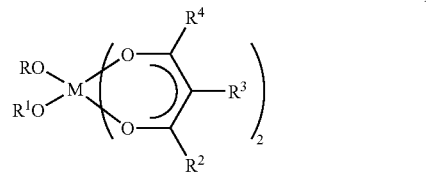

I wherein M comprises a metal chosen from Ti, Zr and Hf; R and $R^1$ are each selected independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are the same alkyl groups; and wherein the at least one of the Group 4 metal-containing precursor having formula I is selected from the group consisting of bis(ethoxy)bis(2,2,6,6-tetramethyl-3,5-heptanedionato)titanium, (ethoxy)(isoproxy)bis(2,2,6,6-tetramethyl-3,5-heptanedionato)titanium, and bis(iso-propoxy)bis(2,2,6,6-tetramethyl-3,5-heptanedionato)titanium.

18. A method for forming a metal-containing film on at least a surface of a substrate comprising:
forming via vapor deposition the metal-containing film on the surface from a composition comprising Group 4 metal-containing precursor having the following formula I:

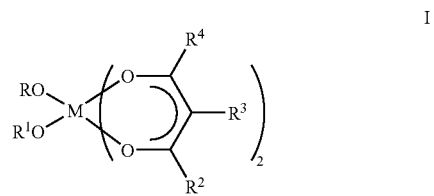

I wherein M comprises a metal chosen from Ti, Zr and Hf; R and $R^1$ are each independently selected from an alkyl group comprising from 1 to 10 carbon atoms; $R^2$ is an alkyl group comprising from 1 to 10 carbon atoms; $R^3$ is chosen from hydrogen or an alkyl group comprising from 1 to 3 carbon atoms; $R^4$ is an alkyl group comprising from 1 to 6 carbon atoms and wherein $R^2$ and $R^4$ are different alkyl groups; and wherein the at least one of the Group 4 metal-containing precursor having formula I is selected from the group consisting of bis(iso-propoxy)bis(2,2-dimethyl-3,5-hexanedionato)titanium, (iso-proxy)(n-butoxy)bis(2,2-dimethyl-3,5-hexanedionato)titanium, and bis(n-butoxy)bis(2,2-dimethyl-3,5-hexanedionato)titanium.

* * * * *